(12) United States Patent
Cella et al.

(10) Patent No.: US 7,652,126 B2
(45) Date of Patent: Jan. 26, 2010

(54) MONOMERS AND POLYMERS COMPRISING CONJUGATED GROUPS AND METHODS FOR MAKING THEREOF

(75) Inventors: James Anthony Cella, Clifton Park, NY (US); Joseph John Shiang, Niskayuna, NY (US); Christian Maria Anton Heller, Albany, NY (US); Kyle Erik Litz, Ballston Spa, NY (US); Jie Liu, Niskayuna, NY (US); Larry Neil Lewis, Scotia, NY (US); Gautam Parthasarathy, Saratoga Springs, NY (US); Anil Raj Duggal, Niskayuna, NY (US); David Andrew Simon, Johnstown, NY (US)

(73) Assignee: General Electric Company, Niskayuna, NY (US)

( * ) Notice: Subject to any disclaimer, the term of this patent is extended or adjusted under 35 U.S.C. 154(b) by 299 days.

(21) Appl. No.: 11/170,423

(22) Filed: Jun. 29, 2005

(65) Prior Publication Data
US 2005/0256290 A1   Nov. 17, 2005

Related U.S. Application Data

(63) Continuation-in-part of application No. 10/680,470, filed on Oct. 7, 2003, now abandoned.

(51) Int. Cl.
*C08G 65/38* (2006.01)
*C08G 61/00* (2006.01)
(52) U.S. Cl. ........................................ 528/219; 528/397
(58) Field of Classification Search ................. 528/397, 528/219
See application file for complete search history.

(56) References Cited

U.S. PATENT DOCUMENTS

| | | | |
|---|---|---|---|
| 4,539,507 A | 9/1985 | VanSlyke et al. | |
| 4,640,975 A * | 2/1987 | Matsuo et al. | 528/211 |
| 4,806,443 A * | 2/1989 | Yanus et al. | 430/56 |
| 4,806,444 A * | 2/1989 | Yanus et al. | 430/56 |
| 4,871,634 A * | 10/1989 | Limburg et al. | 430/58.6 |
| 4,985,528 A * | 1/1991 | Mignani et al. | 528/59 |
| 5,041,514 A | 8/1991 | Webb et al. | |
| 5,115,372 A * | 5/1992 | Hampl et al. | 361/323 |

(Continued)

FOREIGN PATENT DOCUMENTS

EP      0 686 662      11/2002

(Continued)

OTHER PUBLICATIONS

Bernius et al., "Progress with Light-Emitting Polymers", Advanced Materials, vol. 12, No. 23, pp. 1737-1750 (Dec. 1, 2000).

(Continued)

*Primary Examiner*—Harold Y. Pyon
*Assistant Examiner*—Liam J Heincer
(74) *Attorney, Agent, or Firm*—Mary Louise Gioeni

(57) ABSTRACT

Disclosed is a polymer composition derived from a bis-phenol comprising a conjugated aromatic radical, optionally comprising nitrogen. Suitable bis-phenols as well as methods for making said polymer are also disclosed. Also disclosed are electroactive layers comprising said polymer and electroactive devices comprising said layer.

15 Claims, 7 Drawing Sheets

U.S. PATENT DOCUMENTS

| | | | | |
|---|---|---|---|---|
| 5,140,093 A * | 8/1992 | Gupta et al. | ................. | 528/193 |
| 5,145,936 A * | 9/1992 | Mercer | ................. | 528/86 |
| 5,247,190 A | 9/1993 | Friend et al. | | |
| 5,268,444 A * | 12/1993 | Jensen et al. | ................. | 528/125 |
| 5,412,059 A * | 5/1995 | Connell et al. | ................. | 528/183 |
| 5,534,613 A * | 7/1996 | Tan et al. | ................. | 528/176 |
| 5,648,448 A * | 7/1997 | Marrocco et al. | ................. | 528/125 |
| 5,708,130 A | 1/1998 | Woo et al. | | |
| 5,736,285 A * | 4/1998 | Nukada et al. | ................. | 430/83 |
| 5,747,175 A * | 5/1998 | Dietz et al. | ................. | 428/480 |
| 5,776,374 A * | 7/1998 | Newsham et al. | ................. | 252/582 |
| 5,874,516 A * | 2/1999 | Burgoyne et al. | ................. | 528/219 |
| 5,994,425 A * | 11/1999 | Narang et al. | ................. | 522/35 |
| 6,025,102 A * | 2/2000 | Pai et al. | ................. | 430/58.8 |
| 6,034,206 A * | 3/2000 | Yamamoto et al. | ................. | 528/397 |
| 6,169,163 B1 | 1/2001 | Woo et al. | | |
| 6,174,636 B1 * | 1/2001 | Fuller et al. | ................. | 430/58.7 |
| 6,255,447 B1 | 7/2001 | Woo et al. | | |
| 6,340,528 B1 * | 1/2002 | Hsieh et al. | ................. | 428/412 |
| 6,353,083 B1 | 3/2002 | Inbasekaran et al. | | |
| 6,380,347 B1 * | 4/2002 | Lau et al. | ................. | 528/219 |
| 6,420,511 B1 * | 7/2002 | Kharul et al. | ................. | 528/176 |
| 6,593,450 B2 * | 7/2003 | Woo et al. | ................. | 528/397 |
| 6,630,562 B2 * | 10/2003 | Ogawa et al. | ................. | 528/196 |
| 6,824,642 B2 * | 11/2004 | Walter et al. | ................. | 156/331.5 |
| 6,914,119 B2 * | 7/2005 | Yoshida et al. | ................. | 528/219 |
| 7,056,633 B2 * | 6/2006 | Kawamura et al. | ................. | 430/59.6 |
| 7,147,906 B2 * | 12/2006 | Herrmann et al. | ................. | 428/64.1 |
| 7,323,533 B2 * | 1/2008 | Becker et al. | ................. | 528/86 |
| 2001/0026878 A1 * | 10/2001 | Woo et al. | ................. | 428/690 |
| 2002/0091200 A1 * | 7/2002 | Angiolini et al. | ................. | 525/199 |
| 2002/0177687 A1 * | 11/2002 | Noguchi et al. | ................. | 528/498 |
| 2003/0175603 A1 * | 9/2003 | Nakata et al. | ................. | 430/58.1 |
| 2003/0203128 A1 * | 10/2003 | Shundo | ................. | 428/1.1 |
| 2004/0044161 A1 * | 3/2004 | Nagashima et al. | ................. | 528/4 |
| 2004/0097699 A1 * | 5/2004 | Holmes et al. | ................. | 528/380 |
| 2004/0166427 A1 * | 8/2004 | Tong et al. | ................. | 430/66 |
| 2005/0064231 A1 | 3/2005 | Towns et al. | | |
| 2005/0075473 A1 | 4/2005 | Cella | | |
| 2006/0154384 A1 * | 7/2006 | Murphy et al. | ................. | 438/7 |
| 2007/0100170 A1 * | 5/2007 | Murase et al. | ................. | 568/633 |
| 2007/0225454 A1 * | 9/2007 | Lewis et al. | ................. | 525/479 |

FOREIGN PATENT DOCUMENTS

| | | |
|---|---|---|
| EP | 1323762 A2 | 12/2002 |
| WO | WO 90/13148 | 11/1990 |
| WO | WO 92/03490 | 3/1992 |
| WO | WO 00/53656 | 9/2000 |

OTHER PUBLICATIONS

Miteva et al., "Improving the Performance of Polyfluorene-Based Organic Light-Emitting Diodes via End-Capping", Advanced Materials, vol. 18, No. 8, pp. 565-570 (Apr. 18, 2001).

Scherf et al., "Semiconducting Polyfluorenes- Towards Reliable Structure-Property Relationships", Advanced Materials, vol. 14, No. 7, pp. 477-487 (Apr. 4, 2002).

Schmitt et al., "Conjugated Polyfluorene/Polyaniline Block Copolymers", Macromolecular Rapid Communications, vol. 22, No. 8, pp. 624-628 (2001).

PCT/US2006/024113 Dated Oct. 27, 2006.

Cella et al., "Synthesis and Electro-optical Properties of Copolymers Derived from Phenol Functional Telechelic Oligofluorenes" in the GE Technical Information Series as 2005 GRC401, Aug. 2005.

Burnell et al., "Synthesis and Electro-optical Properties of Copolymers Derived from Phenol Functional Telechelic Oligofluorenes", Macromolecules, vol. 38, pp. 10667-10677 (2005).

* cited by examiner

MONOMERS AND POLYMERS COMPRISING CONJUGATED GROUPS AND METHODS FOR MAKING THEREOF

CROSS REFERENCE TO RELATED APPLICATIONS

This application is a Continuation-In-Part of U.S. patent application Ser. No. 10/680,470, entitled "Telechelic Emissive Oligomers and Polymers Derived therefrom", filed Oct. 7, 2003 now abandoned, which is herein incorporated by reference.

BACKGROUND OF THE INVENTION

The present invention is directed to monomers, oligomers and polymers comprising conjugated groups, methods for making thereof, and electroactive layers and devices comprising said polymers.

Electroactive devices are those in which the constituent materials' electronic properties change with respect to the environment and whose changes can be effectively used to convert one form of energy to another. Suitable examples of electroactive devices include, but are not limited to, photovoltaic devices, electroluminescent devices, electro-optical devices, and the like. Electroluminescent devices are structures that emit light when subjected to an applied electric field. In its simplest form, an electroluminescent device comprises a light-emissive layer between two electrodes. The cathode electrode injects negative charge carriers (electrons) and the anode electrode injects positive charge carriers (holes) into the light-emissive layer. Light emission occurs when the electrons and holes combine in the light-emissive layer to generate photons. As a practical aspect one of the electrodes is typically transparent, to allow the photons to escape the device. The light-emissive layer typically comprises a light-emissive material, often an organic material, which may be laid down as a film without substantially affecting the luminescent characteristics of the material and which is stable at the operational temperature of the device.

The color of the light generated by the light-emissive material is determined by the optical gap or bandgap of the organic light-emissive material, that is to say the difference in energy between the "highest occupied molecular orbital" (HOMO) and the "lowest unoccupied molecular orbital" (LUMO) levels. Effectively, the bandgap is the energy difference or energy gap between the valence band and conduction band. These energy levels can be estimated by photo-emission measurements and measurements of the electrochemical potentials for oxidation and reduction. The level of these energies is affected by numerous factors. Accordingly, the use of such energy values is indicative rather than quantitative.

Organic electroluminescent devices which use an organic material as the light-emissive material are known in the art. Among organic materials, simple aromatic molecules such as anthracene, perylene and coronene are known to show electroluminescence. U.S. Pat. No. 4,539,507 discloses the use of small molecule organic materials as the light-emissive material. Polymers are advantageous over small molecules when used in electroluminescent devices because polymer devices can be made on flexible substrates, and layers of the polymer may be put down by economical coating methods.

WO 90/13148 discloses an electroluminescent device comprising a light-emissive layer which is a polymer film comprising at least one conjugated polymer. In this case, the polymer film comprises a poly (para-phenylene vinylene) (PPV) film.

It is known to use a semiconductive conjugated polymer as the light-emissive layer in an electroluminescent device, for example from EP 0544795. EP 0686662 discloses a device for emitting green light. The anode is a layer of transparent indium-tin oxide. The cathode is a LiAl layer. Between the electrodes is a light-emissive layer of PPV. The device comprises also a hole transport layer of polyethylene dioxythiophene (PEDOT) which provides an intermediate energy level which aids the holes injected from the anode to reach the HOMO level in the PPV.

Polyphenylenes, polyfluorenes and other conjugated aromatic polymers are also well known as active layers in electroluminescent devices. Their synthesis and properties are given in, for example, U. Scherf et al., Adv. Mater., 14 (7), 477 (2002); and M. T. Bernius et al., Adv. Mater., 12 (23), 1737 (2000). These polymeric materials are generally prepared using aromatic coupling reactions, such as the Suzuki or Stille coupling, or the nickel catalyzed coupling reactions of aryl halides. Although the methodology for preparing these polymers has been well established, in many cases the coupling-polymerization reactions afford by-products that limit the molecular weight and may either quench fluorescence or induce significant red shifts in the emission spectrum of the polymer, thus limiting the color tunability of the corresponding electroluminescent devices. There is a need in the art to develop more versatile materials for applications in electroactive devices, which materials can be obtained economically in high yield.

BRIEF DESCRIPTION OF THE INVENTION

The present inventors have discovered versatile monomers and corresponding oligomers and polymers that may be advantageously employed in electroactive devices. In various embodiments the electroactive properties and particularly the light-emissive properties of the oligomers and polymers can be readily varied to achieve desirable processability characteristics, change in color emission, emission efficiency and charge transport properties. Further, the conjugation length of the oligomers and polymers can be readily tailored and the polymerization chemistry can be selected to minimize side reactions, maximize molecular weight control and tailor physical properties of the final polymer. Thus, in one aspect the invention provides a polymer comprising structural units derived from the reaction of (i) a bis-phenol having the formula (I):

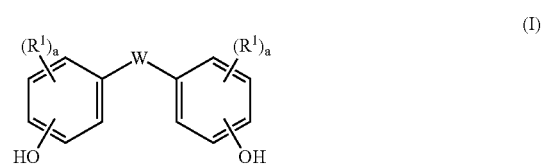

wherein W is a conjugated aromatic radical optionally comprising nitrogen; $R^1$ is independently in each instance an aliphatic radical, an aromatic radical or a cycloaliphatic radical; 'a' is an integer having a value ranging from 0 to 4; and (ii) a second compound selected from the group consisting of:

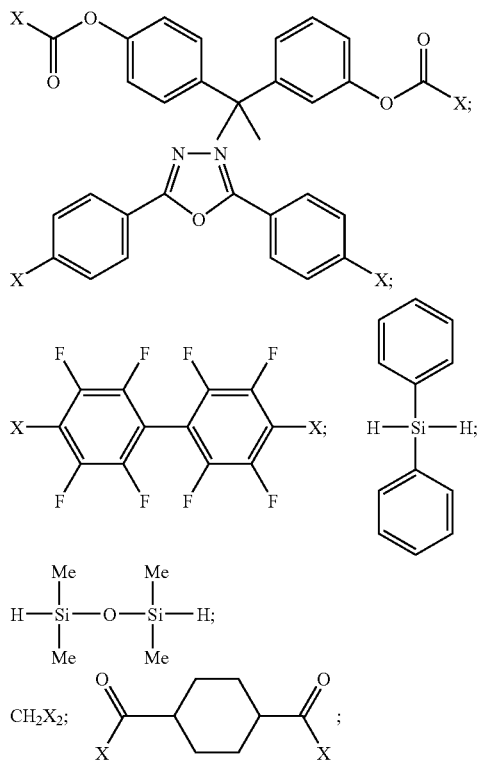

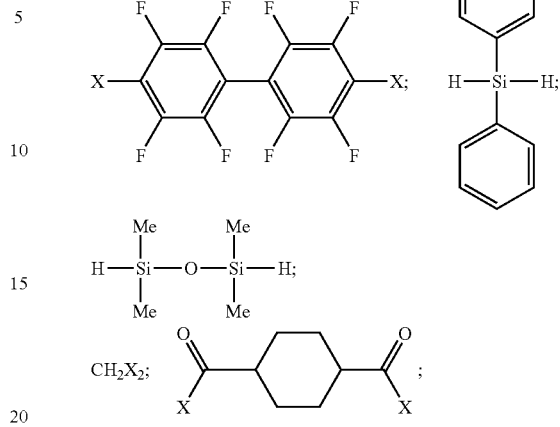

and combinations of any of the aforementioned compounds; wherein X is a halogen radical.

In another aspect the invention provides a method for making a polymer, said method comprising the steps of reacting:
(i) a bis-phenol having the formula (II):

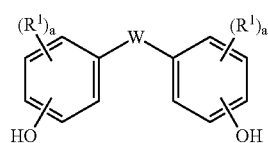
(II)

wherein W is a conjugated aromatic radical optionally comprising nitrogen; $R^1$ is independently in each instance an aliphatic radical, an aromatic radical or a cycloaliphatic radical; 'a' is an integer having a value ranging from 0 to 4; with
(ii) a second compound selected from the group consisting of

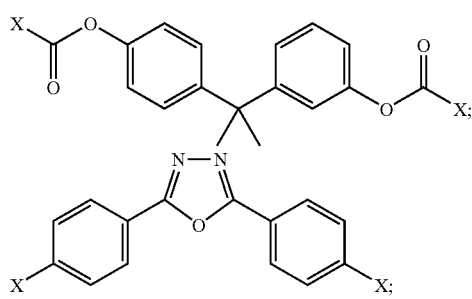

and combinations of any of the aforementioned compounds; wherein X is a halogen radical.

In another aspect the invention provides a bis-phenol monomer having the formula (I):

(I)

wherein W is a conjugated aromatic radical optionally comprising nitrogen; $R^1$ is independently in each instance an aliphatic radical, an aromatic radical or a cycloaliphatic radical; and 'a' is an integer having a value ranging from 0 to 4.

In other embodiments the invention relates to electroactive layers comprising polymers described herein and electroactive devices comprising said layers. Various other features, aspects, and advantages of the present invention will become more apparent with reference to the following description and appended claims.

DETAILED DESCRIPTION OF THE INVENTION

Figure 1:
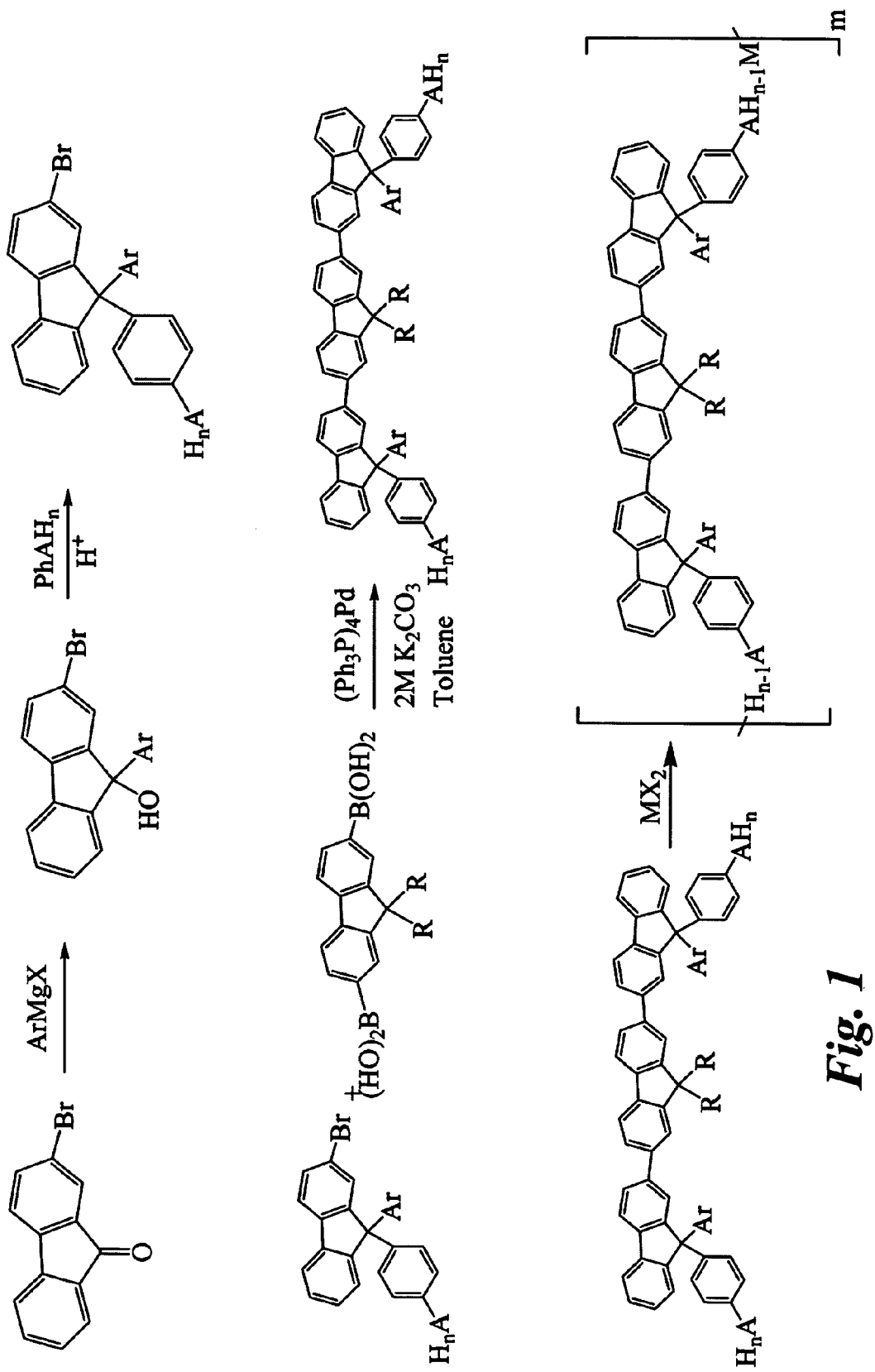
FIG. 1 illustrates in a schematic format one embodiment of a process for preparing some oligomers and polymers of the invention.

In the following specification and the claims which follow, reference will be made to a number of terms which shall be defined to have the following meanings. The singular forms "a", "an" and "the" include plural referents unless the context clearly dictates otherwise.

As used herein the term "aliphatic radical" refers to an organic radical having a valence of at least one comprising a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g. —CH₂CHBrCH₂—), and the like. Further examples of aliphatic radicals include allyl, aminocarbonyl (i.e. —CONH₂), carbonyl, dicyanoisopropylidene (i.e. —CH₂C(CN)₂CH₂—), methyl (i.e. —CH₃), methylene (i.e. —CH₂—), ethyl, ethylene, formyl (i.e. —CHO), hexyl, hexamethylene, hydroxymethyl (i.e. —CH₂OH), mercaptomethyl (i.e. —CH₂SH), methylthio (i.e. —SCH₃), methylthiomethyl (i.e. —CH₂SCH₃), methoxy, methoxycarbonyl (i.e. CH₃OCO—), nitromethyl (i.e. —CH₂NO₂), thiocarbonyl, trimethylsilyl (i.e. (CH₃)₃Si—), t-butyldimethylsilyl, trimethoxysilylpropyl (i.e. (CH₃O)₃SiCH₂CH₂CH₂—), vinyl, vinylidene, and the like. By way of further example, a $C_1$-$C_{10}$ aliphatic radical contains at least one but no more than 10 carbon atoms. A methyl group (i.e. CH₃—) is an example of a $C_1$ aliphatic radical. A decyl group (i.e. CH₃(CH₂)₉—) is an example of a $C_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —(CH₂)₄—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as trifluoromethylphenyl, hexafluoroisopropylidenebis(4-phen-1-yloxy) (i.e. —OPhC(CF₃)₂PhO—), chloromethylphenyl; 3-trifluorovinyl-2-thienyl; 3-trichloromethylphen-1-yl (i.e. 3-CCl₃Ph-), 4-(3-bromoprop-1-yl)phen-1-yl (i.e. BrCH₂CH₂CH₂Ph-), and the like. Further examples of aromatic radicals include 4-allyloxyphen-1-oxy, 4-aminophen-1-yl (i.e. H₂NPh-), 3-aminocarbonylphen-1-yl (i.e. NH₂COPh-), 4-benzoylphen-1-yl, dicyanoisopropylidenebis (4-phen-1-yloxy) (i.e. —OPhC(CN)₂PhO—), 3-methylphen-1-yl, methylenebis(phen-4-yloxy) (i.e. —OPhCH₂PhO—), 2-ethylphen-1-yl, phenylethenyl, 3-formyl-2-thienyl, 2-hexyl-5-furanyl; hexamethylene-1,6-bis(phen-4-yloxy) (i.e. —OPh(CH₂)₆PhO—); 4-hydroxymethylphen-1-yl (i.e. 4-HOCH₂Ph-), 4-mercaptomethylphen-1-yl (i.e. 4-HSCH₂Ph-), 4-methylthiophen-1-yl (i.e. 4-CH₃SPh-), 3-methoxyphen-1-yl, 2-methoxycarbonylphen-1-yloxy (e.g. methyl salicyl), 2-nitromethylphen-1-yl (i.e. —PhCH₂NO₂), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e. —$C_6H_{10}C(CF_3)_2$ $C_6H_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 4-allyloxycyclohex-1-yl, 4-aminocyclohex-1-yl (i.e. $H_2NC_6H_{10}$—), 4-aminocarbonylcyclopent-1-yl (i.e. $NH_2COC_5H_8$—), 4-acetyloxycyclohex-1-yl, 2,2-dicyanoisopropylidenebis(cyclohex-4-yloxy) (i.e. —$OC_6H_{10}C(CN)_2C_6H_{10}O$—), 3-methylcyclohex-1-yl, methylenebis(cyclohex-4-yloxy) (i.e. —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) (i.e. —$OC_6H_{10}(CH_2)_6C_6H_{10}O$—); 4-hydroxymethylcyclohex-1-yl (i.e. 4-$HOCH_2C_6H_{10}$—), 4-mercaptomethylcyclohex-1-yl (i.e. 4-$HSCH_2C_6H_{10}$—), 4-methylthiocyclohex-1-yl (i.e. 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e. $NO_2CH_2C_6H$ —), 3-trimethylsilylcyclohex-1-yl, 2-t-butyldimethylsilylcyclopent-1-yl, 4-trimethoxysilylethylcyclohex-1-yl (e.g. $(CH_3O)_3$ $SiCH_2CH_2C_6H$ —), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

In one embodiment this invention is related to polymers comprising conjugated groups. Depending on the nature of the conjugated groups and the final product that is made using these polymers, the conjugated groups on the polymers may be referred to by various terms. In one non-limiting embodiment, conjugated groups may be referred to as emissive segments. In another non-limiting embodiment, conjugated groups may also be referred to as charge transport segments. In yet another non-limiting embodiment, conjugated groups may also be referred to as charge blocking segments. The polymers are derived from bis-functional compounds represented by formula (II):

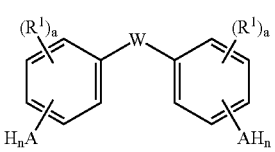

(II)

wherein W is a conjugated aromatic radical optionally comprising nitrogen; $R^1$ is independently in each instance an aliphatic radical, an aromatic radical or a cycloaliphatic radical; 'a' is an integer having a value ranging from 0 to 4; "A" is selected from the group consisting of O, N, and S; and "n" is an integer having a value of 1 or 2.

Figure 2:
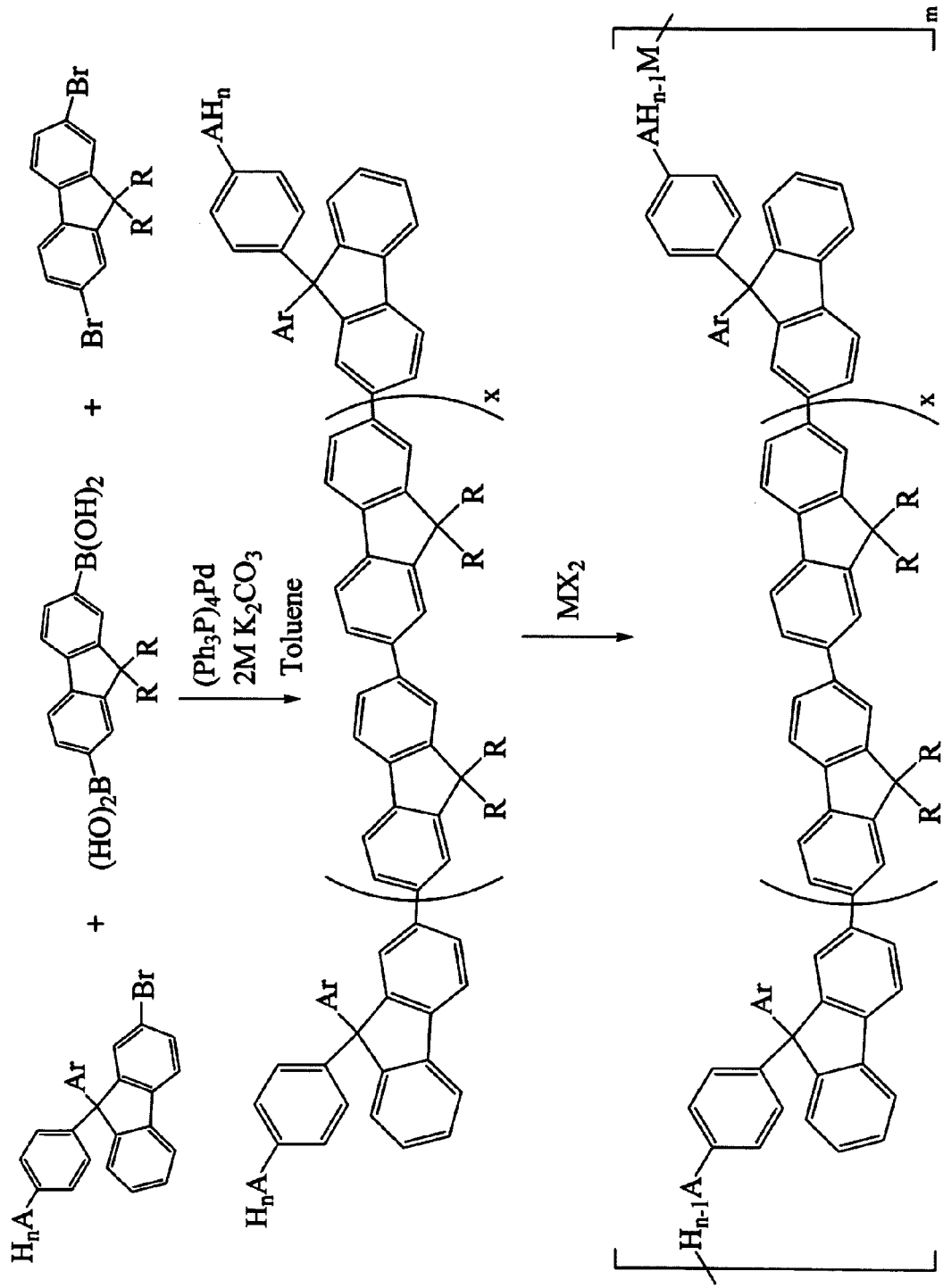
FIG. 2 illustrates in a schematic format another embodiment of a process for preparing some oligomers and polymers of the invention.

In one particular embodiment the present invention relates to the reaction of a first compound comprising a phenol, thiol or amine functional moiety, which is substituted with either an aryl halide or an aryl boronic acid or ester, with a second compound comprising either a bis-boronic acid or ester, or a bis-haloarene using Suzuki coupling conditions to form phenol, thiol or amine end-functionalized conjugated oligomers of polyarylenes. Illustrative examples of particular methods for preparing some particular monomers, oligomers, and polymers of the invention are illustrated in FIG. 1 and FIG. 2. In each of these schemes, Ar represents any aromatic moiety; the moiety "A" can be oxygen, sulfur or nitrogen; the parameter "n" is 1 or 2 depending on the identity of A; the moiety "R" may be, independently in each occurrence, aliphatic, cycloaliphatic, or aromatic; and the parameter "m" may have a value of about 1 to about 1000, and more preferably, "m" may have a value of about 1 to about 250. In FIG. 2 the parameter "x" may have a value of 0 to about 100 in one embodiment and a value of 1 to about 50 in another embodiment.

Additionally, Ar and the aryl ring bearing the moiety A as shown in FIG. 1 may be connected to each other by a carbon-carbon or carbon-heteroatom bond in spiro structures, such as in the illustrative part structures of the following formulas (AA), wherein aromatic rings may be substituted or unsubstituted and wherein "$X^2$," is NR, O, or S, and the moiety R may be aliphatic, cycloaliphatic, or aromatic:

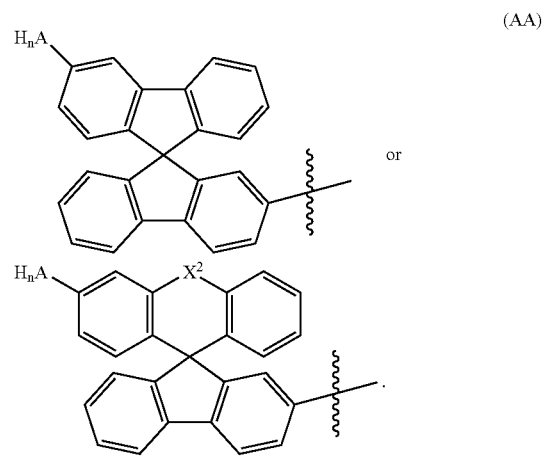

(AA)

Likewise, the R groups as shown in FIG. 1 may be linked together in spiro structures as in the following illustrative part structure (BB), wherein aromatic rings may be substituted or unsubstituted:

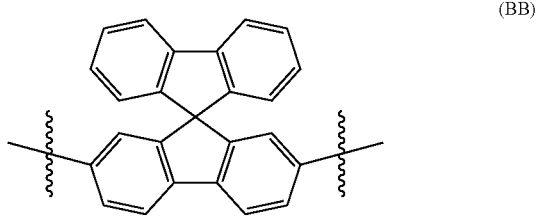
(BB)

Figure 3:
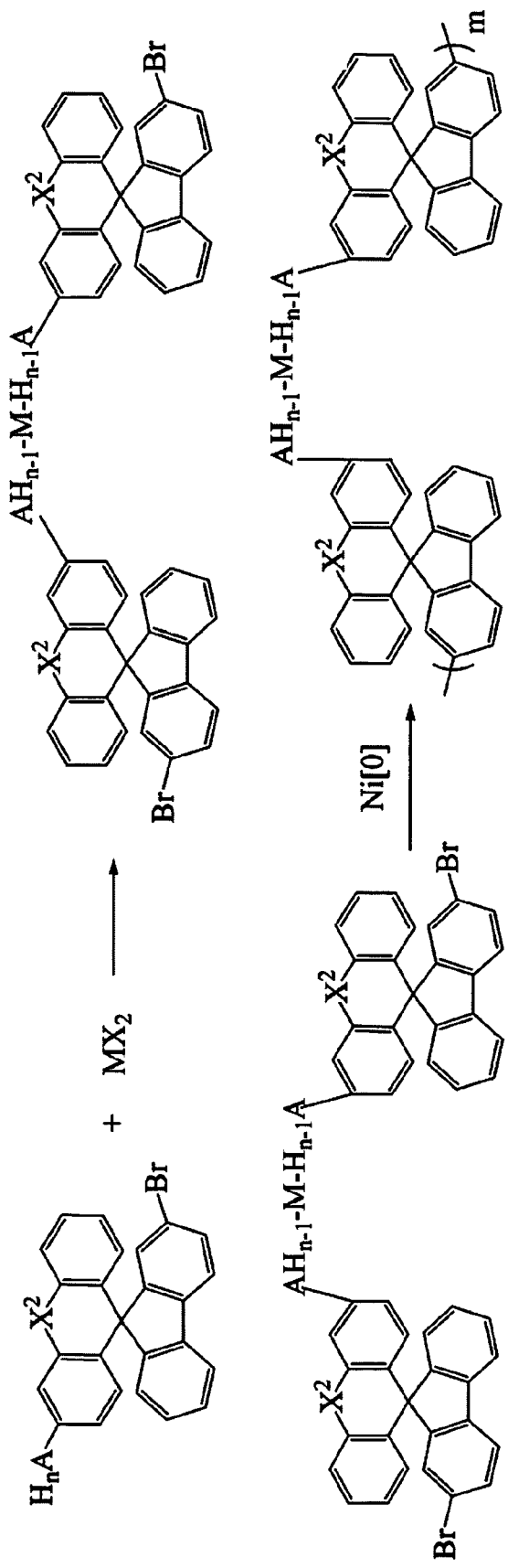
FIG. 3 illustrates in a schematic format another embodiment of a process for preparing some oligomers and polymers of the invention.

In addition, compounds may be employed which have the following structure (CC), wherein aromatic rings may be substituted or unsubstituted; the moiety "A" can be oxygen, sulfur or nitrogen; the parameter "n" is 1 or 2 depending on the identity of A; the moiety R may be aliphatic, cycloaliphatic, or aromatic; and the parameter "x" may have a value of 0 to about 100 in one embodiment and a value of 1 to about 50 in another embodiment:

moiety "R" may be, independently in each occurrence, aliphatic, cycloaliphatic, or aromatic; and the moiety "$X^2$" is a single bond, NR, O, or S. In FIG. 3 the parameter "m" may have a value of about 1 to about 1000, more preferably, "m" may have a value of about 1 to about 250. The compound $MX_2$ in each of FIGS. 1, 2 and 3 is any difunctional, organic monomer capable of reacting with the moiety $AH_n$ to form a homopolymer or copolymer. Examples of $Mx_2$ include, but are not limited to, BPA-bis-chloroformate, terephthalic acid or its diacid chloride or diester, dichlorophenylsulfone, pyromellitic dianhydride, adipoylchloride, diphenyldichlorosilane, dimethyldichlorosilane, 1,1,3,3-tetramethyldisiloxane, phosgene and the like, and mixtures thereof. The aromatic rings of compounds shown in FIGS. 1, 2 and 3 may be substituted or unsubstituted.

The term "homopolymer" in some embodiments of the present invention refers to polymeric structures wherein the electroactive segments are linked together solely by the linker $MX_2$. The term "copolymer" in some embodiments of the present invention refers to polymeric structures wherein one or more electroactive segments and/or one or more non-electroactive segments are linked together by the linker $Mx_2$. The

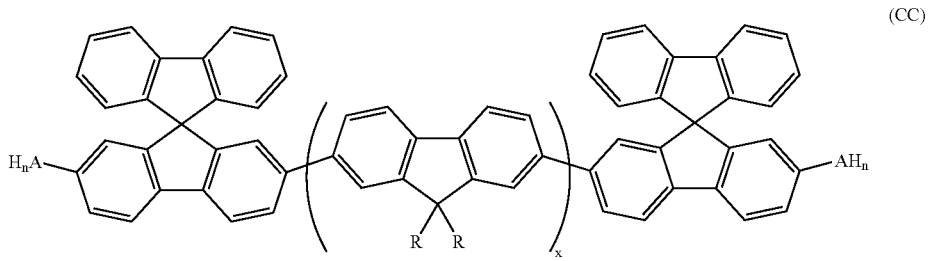
(CC)

Furthermore, some of the polymers of the present invention may be obtained by first linking the A moiety functional components together via a carbonate, or other suitable linkage, and then polymerizing through an aryl halide functionality using typical aryl coupling chemistry as is shown in an illustrative embodiment in the scheme of FIG. 3. In FIG. 3 the moiety "A" can be oxygen, sulfur or nitrogen, and the parameter "n" is 1 or 2 depending on the identity of A. In FIG. 3 the link segments in a copolymer can be dispersed randomly or in an alternating manner.

In some particular embodiments suitable monomers comprise those represented by the bis-phenol compound (I) wherein "A" is oxygen and the parameter "n" is equal to one. Exemplary bis-phenol compounds comprising conjugated units, in addition to those cited herein above, comprise: (a) those of the formula (IIIa):

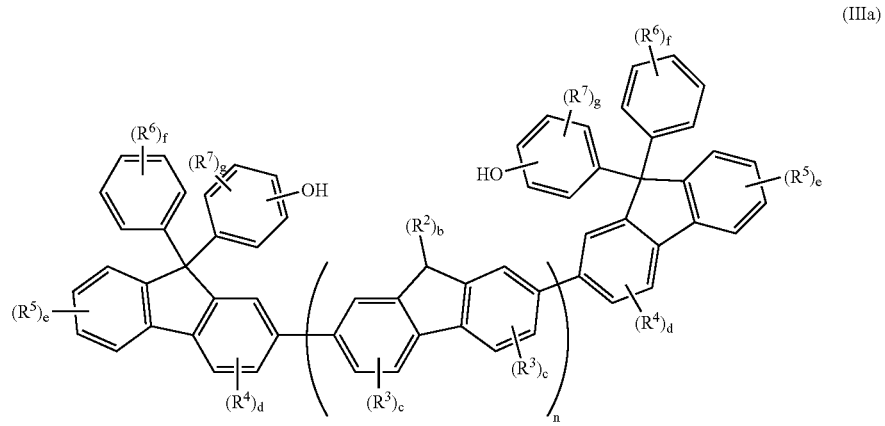
(IIIa)

wherein $R^2$, $R^3$, $R^4$, $R^5$, $R^6$, and $R^7$ are independently in each instance, an aliphatic, an aromatic or a cycloaliphatic radical, 'b' is an integer having a value 0, 1, or 2; 'c' is an integer having a value ranging from 0 to 3; 'd' is an integer having a value ranging from 0 to 3; 'e' is an integer having a value ranging from 0 to 4; 'f' is an integer having a value ranging from 0 to 5; 'g' is an integer having a value ranging from 0 to 4; and 'n' is a number ranging from 0 to 100;

(b) those of the formula (IIIb):

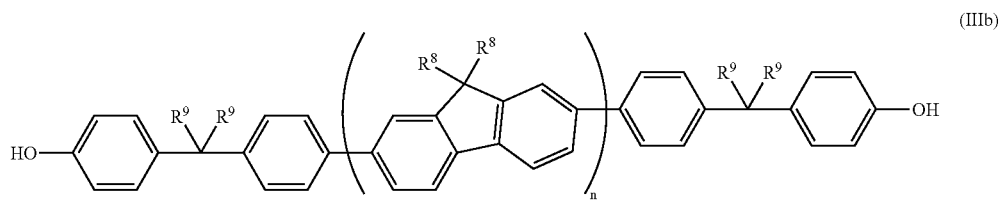

wherein $R^8$ and $R^9$ are independently in each instance, an aliphatic, an aromatic or a cycloaliphatic radical, particularly an aliphatic radical of the formula $C_xH_{2x-1}$, and more particularly wherein $R^8$ is $C_6H_{13}$ and wherein $R^9$ is $CH_3$; and 'n' is a number ranging from 1 to 100;

(c) those of the formula (IIIc):

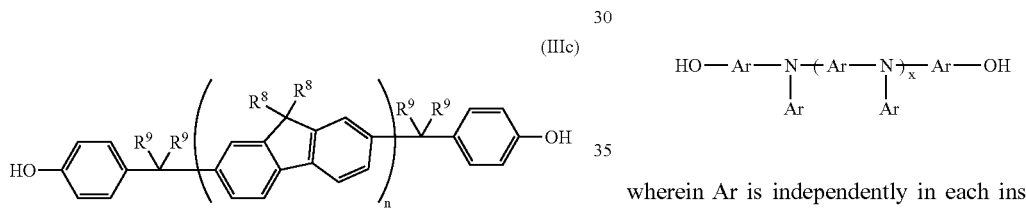

wherein $R^8$ and $R^9$ are independently in each instance, an aliphatic, an aromatic or a cycloaliphatic radical, particularly an aliphatic radical of the formula $C_xH_{2x-1}$, and more particularly wherein $R^8$ is $C_6H_{13}$ and wherein $R^9$ is $CH_3$; and 'n' is a number ranging from 1 to 100;

(d) those of the formula:

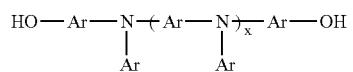

wherein Ar is independently in each instance an aromatic radical; and 'x' is an integer ranging from 0 to 10;

(e) those of the formulas:

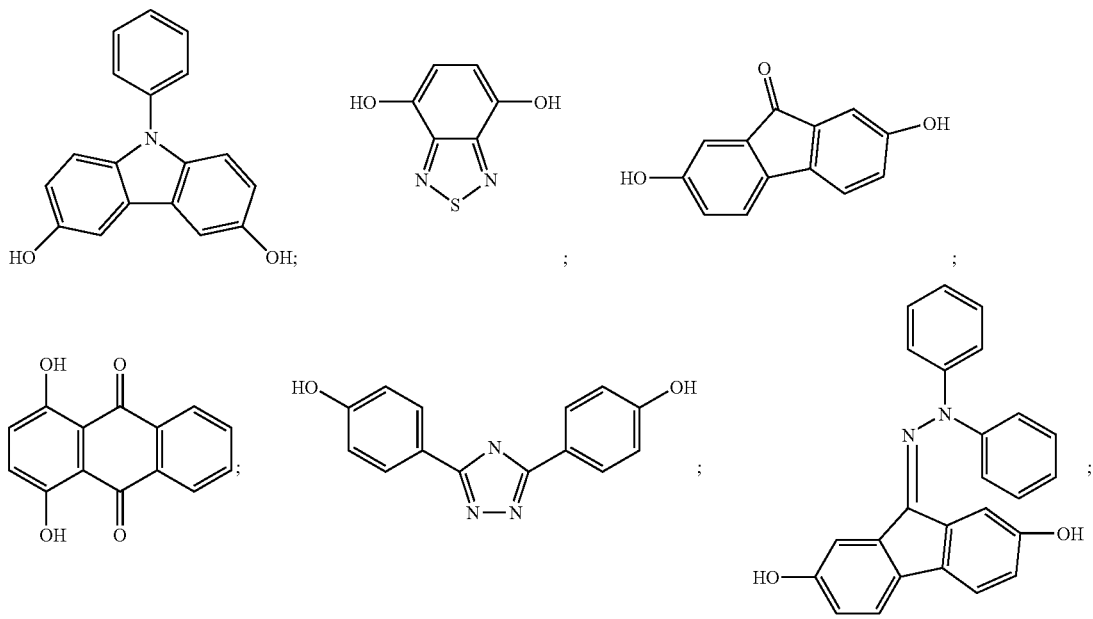

-continued

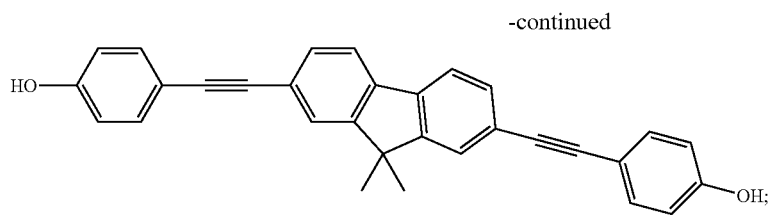 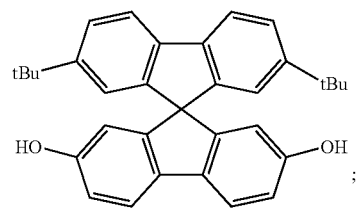

or (f) combinations of any of the aforementioned compounds.

When bis-phenol compounds are employed in this invention, then typically they are either commercially available or are synthesized by the Suzuki or Stille coupling reactions, which are widely known and used to form carbon-carbon linkages, especially for the synthesis of conjugated systems and aromatic-aromatic linkages. Such reactions are typically conducted between organoboron reagents comprising conjugated groups and organohalides comprising conjugated groups. Suitable organoboron reagents comprise those comprising boronic esters and those comprising boronic acids.

Organoboron reagents used in the coupling reactions are typically synthesized by the reaction of organolithium reagents with trialkoxy borates, followed by acidification. Alternate methods include reacting Grignard reagents such as organomagnesium halides with trialkoxy borates or trialkyl borates. These reactions are typically conducted in ethereal solvents such as diethyl ether, dimethyl ether, diglyme, glyme, tetrahydrofuran, and the like. An alternate method of obtaining organoboron reagents is by the cross-coupling reaction of an organic halide with an organoboron compound. This cross-coupling reaction is known to be tolerant to a wide variety of functional groups. Some exemplary organoboron compounds include, but are not limited to, isopropoxypinacolato diboron, bis-pinacolato diboron, disiamyl borane, and thexyl borane. This reaction may be conducted in polar solvents such as dimethyl formamide, dimethyl sulfoxide, tetrahydrofuran, and the like; or in non-polar solvents such as toluene, benzene, hexane, heptane, carbon tetrachloride, and the like. Metal complex catalysts may be employed advantageously in the cross-coupling reaction to improve yields and increase the reaction rates. Typical catalysts include palladium complexes such as $PdCl_2$, $Pd(OAc)_2$, and the like. The cross-coupling reaction is conducted at temperatures in the range of from about minus 100° C. to about 150° C., and more preferably in the range of from about 0° C. to about 100° C. The final product may be isolated by standard techniques known to those skilled in the art such as filtration and evaporation of solvent, and further purified by techniques such as chromatography.

The coupling reactions typically involve the reaction of organoboron reagents with organohalides. Organohalides may also be derived from alkenes, alkynes, aromatic compounds, and the like. If the unsaturation on the organohalides is on the alpha carbon with respect to the halogen group, then the reaction gives rise to a conjugated product. The reaction between organoboron reagents and organohalides is typically conducted in the presence of catalysts, most notably palladium catalysts. Other metal complex catalysts comprise Ni(II) complexes, Fe(III) catalysts, and the like. Typical catalysts include palladium complexes such as $PdCl_2$, $Pd(OAc)_2$, and the like. This reaction may be conducted in polar solvents such as dimethyl formamide, dimethyl sulfoxide, tetrahydrofuran, and the like; or in non-polar solvents such as toluene, benzene, hexane, heptane, carbon tetrachloride, and the like.

The reaction is typically conducted at temperatures in the range of from about minus 100° C. to about 150° C., more preferably in the range of from about 0° C. to about 100° C. The final product may be isolated by standard techniques known to those skilled in the art such as filtration and evaporation of solvent, and further purified by techniques such as chromatography.

In a typical embodiment the organohalide used in the coupling reaction is an organodihalide. The organoboron reagent typically comprises at least one hydroxyl or phenolic group and is typically taken in at least a 2:1 molar ratio with respect to the organodihalide. Thus, bis-phenol compounds comprising conjugated groups may be obtained in this manner.

The extent of conjugation is known to affect the bandgap of the conjugated molecule. Increasing the extent of conjugation has the effect of decreasing the bandgap up to the point of bandgap conversion. Therefore, selection of an appropriate molecular structure is one way of selecting the bandgap. This gives the very desirable feature of controlling the color of the light output when the molecule is made to emit light. This property is particularly useful in the construction of electroluminescent devices. In one embodiment of the present invention the conjugation length is varied by synthesizing oligomers comprising different lengths of conjugated units comprising bis-phenol end groups. Oligomers as used herein, are monomers comprising repetitive structural units having functional end groups that are useful for polymerization reactions with other difunctional monomers.

The polymers useful in the invention may be synthesized by reacting the aforementioned compounds of formula (I) with a comonomer. The comonomer used comprises functional groups that are capable of reacting with the nucleophilic groups on compounds of formula (I), such as the hydroxyl groups of the bis-phenol compounds. Exemplary functional groups that react with nucleophilic groups include but are not limited to anhydrides, carboxylic acids, halides, silanes, hydridosiloxanes, haloformates, and the like. Comonomers may also optionally comprise conjugated groups. Typical comonomers are selected from the group consisting of compounds of the formulas:

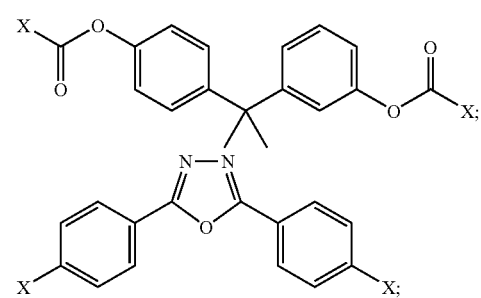

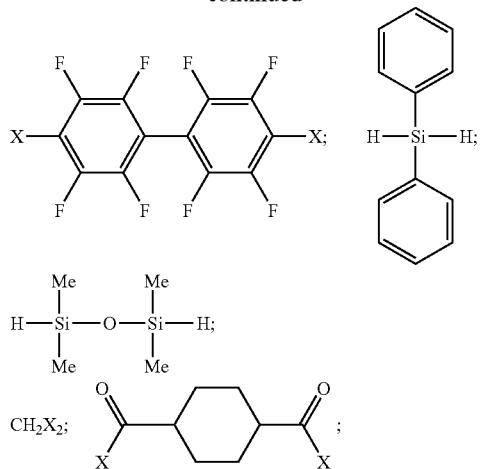

and combinations of any of the aforementioned compounds; wherein X is a halogen radical. Typical linking groups that arise from the reaction of hydroxyl groups on the bis-phenol compounds and the functional groups on the comonomers are esters, ethers, carbonates, silanes, and the like.

Polymerization reactions to form polymers of the invention are advantageously conducted in the presence of a solvent. Solvents may be readily selected based on the identity of the monomers involved. Typical solvents include chlorinated solvents such as dichloromethane, chloroform, 1,2-dichloroethane, and the like; dipolar aprotic solvents such as N-methylpyrrolidinone, dimethyl formamide, dimethyl acetamide, dimethyl sulfoxide, and the like; aromatic solvents such as toluene, chlorobenzene, ortho-dichlorobenzene, xylene, and the like; ether solvents such as THF, dioxane, glyme, and the like. The polymerization reaction is typically conducted in the presence of a suitable catalyst. Typical catalysts used to effect the formation of esters, carbonates, and ethers include bases such as triethylamine, N-methylpyrrolidinone, potassium carbonate, and the like. In one embodiment the solvent used may also act as the catalyst. Typical catalysts used to effect the formation of silanes include Lewis acid catalysts such as tris(pentafluorophenyl)borate.

Solubility of the polymers of the invention may be modulated by the choice of the second compound. Thus, in one embodiment, introducing a polar group in the repeat unit, such as a carbonate linkage, results in a polymer that is soluble in common solvents. This improvement in the solubility characteristics makes it easier to fabricate devices.

Devices from polymers comprising conjugated groups may be fabricated using techniques known to those of ordinary skill in the art. An exemplary method to prepare hole-only devices is as follows: indium-tin-oxide (ITO) coated glass is cleaned, sterilized by exposure to UV light or ozone, coated with a thin layer of a conducting polymer, baked, and then coated with a test polymer by standard methods. A shadow mask is used to vacuum-deposit top electrodes. Subsequently, a film of gold is evaporated onto the surface at a suitable rate. In the case of an electron-only device, typically aluminum is used as the bottom electrode, and a thin layer of sodium fluoride comprising aluminum is used as the top electrode. Several samples with different spin-speeds can be made using spin coating to interpolate for a target value of 50 nm thickness. Finally, electrical contact is established with a thin gold wire mounted to a micro-probe. Variations to the process described herein will be evident to one of ordinary skill the art.

The color tunability of the devices comprising the polymers described in the invention may be further refined by the use of small molecule dyes. The dyes may be incorporated into the polymers using methods known in the art, such as, but not limited to, solution, dispersion, or melt mixing techniques. In a particular embodiment a dye may be incorporated into a polymer by solution blending. Exemplary dyes that may be used in the devices comprise perylene dyes, anthracene dyes, coumarin dyes, stibene dyes, xanthene dyes, oxazine dyes, pyromethane dyes, 4-dicyanmethylene-2-methyl-6-(p-dimethylaminostyryl)-4H-pyran dyes, porphyrinoid dyes, metal complexes of porphyrinoid dyes, and the like. Dyes comprising organic complexes of metals in the lanthanide series having oxidation states +2, +3, or +4 may also be used here. Dyes comprising complexes of transition metals such Os, Ir, Ru, Re, Rh, and the like can be used in conjunction with polymers comprising conjugated groups for various applications. Combinations of the aforementioned dyes are also contemplated for use in a device.

The polymers of this invention have surprisingly been found to show excellent potential for several applications such as, but not limited to electroluminescent devices, electro-optic devices, photovoltaic devices, and the like. The polymers comprising conjugated groups may be used as such. Alternately, in another embodiment it is contemplated that the polymers may be used as part of a blend comprising at least one other polymer. In some illustrative embodiments the polymers described herein may be blended with each other or they may be blended with other electroactive polymers. Exemplary electroactive polymers include, but are limited to poly(thiophene), poly(fluorene), poly(aniline), poly(phenylene), and poly(vinyl phenylene).

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES 2,7-Dibromo-9,9-dihexylfluorene, 9,9-dihexylfluorene-2,7-bis-trimethyleneboronate, fluorenone, palladium acetate, tetraethylammonium hydroxide (20 wt. % aqueous solution) and N-bromosuccinimide were purchased from Aldrich and used without further purification. Tetrakis-triphenylphosphine palladium(0) was either purchased from Aldrich or prepared fresh as described by Coulson, D. R., in Inorganic Syntheses (1990), vol. 28, pp. 107-9. n-Butyllithium (about 1.2 Molar) in hexane was obtained from Aldrich and titrated prior to use using N-pivaloyl-o-toluidine. Decafluorobiphenyl was obtained from TCI America. BPA means bisphenol-A. 3-(Diethylenetriamino)propyl-functionalized silica gel was 200-400 mesh and was obtained from SiliCycle, Quebec City, Quebec, Canada. Test polymers poly(9,9-dioctylfluorenyl-2,7-diyl) (available under the trade name ADS329®) and poly[9,9-di-(2-ethylhexyl)-fluorenyl-2,7-diyl] were purchased from American Dye Source, Inc., Quebec, Canada, and used as received without any further purification. $^1$H NMR spectra were recorded on a Bruker 500 megahertz instrument. UV spectra were recorded on a Varian-Cary 300

Scan UV-Vis spectrophotometer. Gel permeation chromatography was carried out using a Perkin-Elmer Series 200 pump and a Perkin-Elmer 235 Diode Array Detector. Chloroform was used as the eluant at a flow rate of 1.0 milliliters per minute (ml/min) through a MetaChem Technologies, 5 micron linear 300 millimeter (mm)×7.8 mm column. Liquid Chromatography was carried out using a Perkin-Elmer Series 200 pump and UV-Vis detector on a Whatman Partisil 5 ODS-3 10 mm×4.5 mm column eluted with a water-acetonitrile linear gradient (50%-95% vol/vol acetonitrile) at a flow rate of 1.5 ml/min.

Synthesis of 2-Bromofluorenone: Fluorenone (41 grams (g); 0.228 mol) was dissolved in 225 milliliters (ml) of methanesulfonic acid and treated portion wise at room temperature with solid N-bromosuccinimide (NBS) (38.55 g; 0.217 mol). The mixture became dark and warm, and the temperature was maintained below 60° C. by controlling the rate of NBS addition. Upon completion of the NBS addition, the mixture was allowed to cool to room temperature and was poured into 1 liter of ice water. The yellow solid that separated was collected by filtration, washed with copious quantities of water, air dried, and then recrystallized from about 1.5 liters of ethanol. The yield was 40 g (71%) and the product contained 5-10% of 2,7-dibromofluorenone as indicated by LC analysis. A small sample was purified by column chromatography, but in general the contaminated material was carried on in subsequent steps.

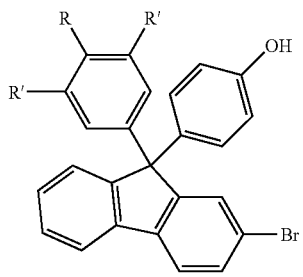

(IVa: R = t-Bu; R' = H)
(IVb: R = H; R' = CF₃)

Example 1

Synthesis of 2-bromo-9-(4-tert-butyl)phenyl-9-(4-hydroxy)phenylfluorene (IVa): Solid 2-bromofluorenone (5.18 g; 20 millimoles (mmol)), was added in portions to the Grignard reagent prepared from 4-bromo-tert-butylbenzene (4.47 g; 21 mmol), 1,2-dibromoethane (1.88 g; 10 mmol), and magnesium (0.753 g; 31 milligram-atoms) in 75 ml of anhydrous ether. The reaction mixture was refluxed for one hour after all the solids had been added. The cooled mixture was quenched by adding 50 ml of saturated ammonium chloride solution. The organic phase was washed with equal volumes of water and saturated NaCl, and was then passed through a cone of anhydrous CaSO₄. Solvent was removed on a rotary evaporator to afford 10 g of an amber oil that was chromatographed on silica gel (about 300 g) eluted with hexane-ethyl acetate to afford 5.64 g (72%) of the desired carbinol as a colorless oil. The mass spectrum and ¹H NMR data showed formation of the desired carbinol. The carbinol (6.0 g; 15 mmol) and phenol (2.2 g; 23.25 mmol) were dissolved in 10 ml of methylene chloride. Methanesulfonic acid (200 microliters; 3.08 mmol) was added and the mixture was stirred at ambient temperature. When the reaction was complete (about 5 min), the organic phase was washed with water and saturated NaCl. Evaporation of solvent afforded an oil that was chromatographed on 200 g of silica gel (hexane-ethyl acetate gradient) to afford 4.4 g (61%) of the product as a colorless oil. The oil could be crystallized by slow evaporation of an ether-hexane solution. The mass spectrum and ¹H NMR data showed formation of the desired product.

Example 2

Synthesis of 2-bromo-9-(3,5-bis-trifluoromethyl)phenyl-9-(4-hydroxy)phenylfluorene, (IVb): Solid 2-bromofluorenone (42 g; 161.5 mmol), dried in a vacuum oven overnight at 65° C. to remove excess ethanol from crystallization, was added via a solid addition funnel in portions to the Grignard reagent prepared from 3,5-bis-trifluoromethylbromobenzene (50 g; 170 mmol), 1,2-dibromoethane (7.36 ml; 85 mmol), and magnesium (6.223 g; 256 milligram-atoms) in a three-neck 1 liter flask filled with 400 ml of anhydrous ether. After 30 minutes, the mixture was quenched by adding an excess of saturated ammonium chloride solution. The organic phase was washed 3 times with equal volumes of water and saturated NaCl, and was then passed through a cone of anhydrous MgSO₄. Solvent was removed on a rotary evaporator to afford a light brown solid. The total mass was dissolved in 800 ml of methylene chloride in a one-neck 1 liter flask along with phenol (24 g; 256 mmol, 1.5 molar excess). Methanesulfonic acid (21.5 ml) was added and the mixture was stirred at ambient temperature for 18 hours. When the reaction was complete, the organic phase was washed with water and saturated NaCl. Evaporation of solvent yielded an off-white solid. The product was further purified by trituration with a minimal amount of methylene chloride and hexanes (20/80 vol/vol). Final yield was 58.9 g (63.6%). The mass spectrum and ¹H NMR data showed formation of the desired product.

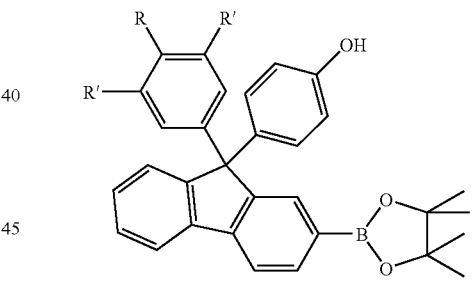

(Va: R = t-Bu; R' = H)
(Vb: R = H; R' = CF₃)

Example 3

Synthesis of 2-(1,1,2,2-tetramethylethyleneboronato)-9-(4-tert-butyl)phenyl-9-(4-hydroxy)phenylfluorene (Va): A mixture of bromide (IVa) (0.469 g; 1.0 mmol), bis-pinacolatodiboron (0.279 g; 1.1 mmol), potassium acetate (0.294 g; 3.0 mmol), palladium(II) acetate (0.0075 g; 0.03 mmol) and DMF (10 ml) was stirred at 80° C. under a positive nitrogen pressure for 5 hr. Additional bis-pinacolatodiboron (0.075 g) and Pd(OAc)₂ (0.002 g) were added, and heating and stirring were continued for an additional 1.5 hr. The mixture was poured into 100 ml of cold water made slightly acidic with HCl. Solids were collected by filtration and stirred with 50 ml ethyl acetate. The solution was filtered through CELITE®, washed with brine and dried by passage through a cone of anhydrous CaSO₄. Evaporation of solvent afforded a residue that was chromatographed on 50 g of silica gel eluted with 10-20% ethyl acetate/hexanes. The main fractions crystallized slowly from an ether-hexane solution. The mass spectrum and $^1$H NMR data showed formation of the desired product.

Example 4

Synthesis of 2-(1,1,2,2-tetramethylethyleneboronato)-9-(3,5-bistrifluoromethyl)phenyl-9-(4-hydroxy)phenylfluorene (Vb): A mixture of bromide (IVb) (5.5 g; 10 mmol), bis-pinacolatodiboron (3.0 g; 12 mmol), potassium acetate (2.9 g; 30 mmol) and palladium(II) acetate (0.075 g; 0.3 mmol) in 25 ml of DMF was stirred in a 75° C. bath for 3 hours. The cooled mixture was poured into 250 ml of water made slightly acidic with HCl. The dark solids that separated were collected by filtration, washed with water, and stirred with 150 ml of ethyl acetate. The resulting slurry was filtered through CELITE® and the filtrate was washed successively with water and brine, then passed through a cone of anhydrous $CaSO_4$. Removal of solvent afforded a dark residue that was chromatographed on 150 g of silica gel eluted with 10-20% ethyl acetate in hexane to afford compound (Vb) as a colorless oil. The mass spectrum and $^1$H NMR data showed formation of the desired product.

Example 5

The following examples describe the synthesis of phenol end-capped polyfluorenes having the generic formula (VI):

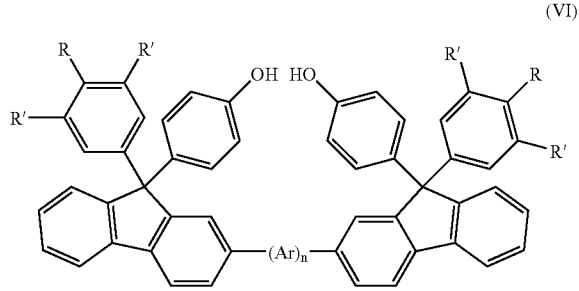

(VI)

Synthesis of phenol functional bifluorene, compound (VIb) with n=0; R═H; R'═CF$_3$: A mixture of phenol borate compound (Vb) (0.596 g; 1.0 mmol), phenol bromide compound (IVb) (0.549 g; 1.0 mmol), toluene (15 ml), and tetraethylammonium hydroxide (0.275 g; 1.4 g of a 20% aqueous solution) was degassed with argon for about 20 minutes. Then tetrakis-triphenylphosphine palladium(0) (0.0035 g; 0.022 mmol) was added and the mixture was stirred under a positive nitrogen pressure at 75° C. for 18 hours. The cooled mixture was diluted with ethyl acetate (25 ml) and 1.0 Normal (1N) hydrochloric acid (25 ml), stirred briefly, then filtered through CELITE®. The organic phase was washed twice with water and once with brine then passed through a funnel containing Drierite on top of a 1 centimeter (cm) layer of 3-(diethylenetriamino)propyl-functionalized silica gel. Removal of solvent in vacuo afforded the product as a white powder.

Example 6

Synthesis of phenol functional bifluorene, compound (VIa) with n=0, R=t-Bu, R'═H: Prepared using basically the same procedure described for the preparation of compound (VIb) in Example 5 from phenol borate compound (Va) and phenol bromide compound (IVa).

Example 7

Synthesis of phenol capped terfluorene, compound (VIb) with Ar=9,9-dihexylfluorene-2,7-diyl, n=1, R═H, R'═CF$_3$: A mixture of phenol bromide compound (IVb) (3.288 g; 6 mmol), 2,7-bis-trimethyleneboronato-9,9-dihexylfluorene (1.266 g; 3 mmol), hexaethylguanidinium chloride (HEGCl; 80 microliters; 0.15 mmol), toluene (150 ml), and 2 Molar (2M) aqueous $K_2CO_3$ solution (25 ml) was degassed with argon for 20 minutes. Then tetrakis-triphenylphosphine palladium(0) (75 milligrams (mg)) was added, and the mixture was immersed in a 110° C. bath. The mixture was stirred under a positive nitrogen pressure for 4.5 hours, then was allowed to cool to room temperature, at which point only one spot was evident via thin layer chromatography. The mixture was treated with 75 mg of 3-(diethylenetriamino)propyl-functionalized silica gel and allowed to stir for half an hour. The mixture was then filtered through CELITE®. The filtrate was washed successively with equal volume of 10% HCl (1×), water (2×), and brine (1×). Evaporation of solvent afforded a residue that was dissolved in ethyl acetate and passed through a short silica gel column eluting with 10-25% vol/vol ethyl acetate-hexane to afford a white solid. The desired product was obtained in a yield of 85%.

Example 8

Synthesis of phenol end-capped terfluorene, compound (VIa) with Ar=9,9-dihexylfluorene-2,7-diyl, n=1, R=t-Bu, R'═H: A mixture of phenol-bromide compound (IVa) (7.74 g; 16.5 mmol), 2,7-bis-trimethyleneboronato-9,9-dihexylfluorene (4.07 g; 8.1 mmol), hexaethylguanidinium chloride (40 mg; 0.15 mmol), and 2M aqueous $K_2CO_3$ (50 ml) and toluene (120 ml) was degassed with argon for 20 minutes. Then tetrakis-triphenylphosphine palladium(0) (0.26 g; 0.225 mmol) was added, and the mixture was immersed in a 110° C. bath. The mixture was stirred under a positive nitrogen pressure for 23 hours, then filtered through CELITE®. The filtrate was washed successively with equal volumes of 10% HCl (1×), water (2×), and brine (1×). The solution was then passed through a fritted filter containing a 5-10 mm layer of 3-(diethylenetriamino)propyl-functionalized silica gel. Evaporation of solvent afforded a residue that was dissolved in ethyl acetate and passed through a short silica gel column to afford 8 g of an orange solid. A 3.0 g sample of this material was chromatographed on 120 g of silica gel (eluting with 10-25% ethyl acetate-hexane) to afford 1.96 g of the desired product.

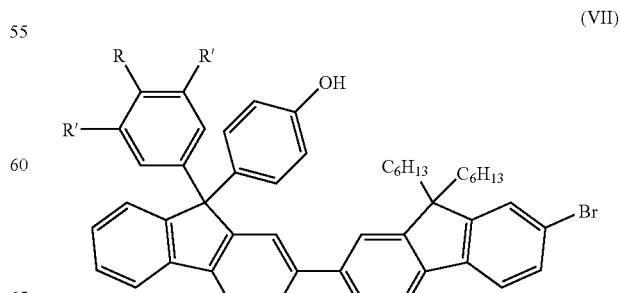

(VII)

Example 9

Synthesis of phenol end-capped pentafluorene, compound (VIb) with Ar=9,9-dihexylfluorene-2,7-diyl, n=3, R=H, R'=CF$_3$: Phenol bromide compound (VII; R=H, R'=CF$_3$) (0.651 g; 0.739 mmol) and 2,7-bis-trimethyleneboronato-9,9-dihexylfluorene (0.178 g; 0.355 mmol) were dissolved in 50 ml of toluene and 15 ml of 2M K$_2$CO$_3$ solution. The solution was degassed with argon for 20 minutes. Then hexaethylguanidinium chloride (40 microliters; 0.075 mmol) was added along with tetrakis-triphenylphosphine palladium(0) (0.008 g; 0.70 mmol). The reaction mixture was heated at 110° C. under nitrogen for 24 hours. The cooled mixture was diluted with 20 ml of 1N HCl and stirred for 10 minutes, then filtered through CELITE®. The aqueous phase was discarded and the organic phase was washed successively with equal volumes of water (3×) and brine (1×). The solution was then passed through a fritted filter containing a 5-10 mm layer of 3-(diethylenetriamino)propyl-functionalized silica gel and anhydrous CaSO$_4$, and then stripped to afford a residue that was chromatographed on silica gel (eluting with 10-25% EtOAc/hexanes) to afford 0.45 g of the product.

Example 10

Synthesis of phenol end-capped heptafluorene, compound (VIb) with Ar=9,9-dihexylfluorene-2,7-diyl, n=5, R=H, R'=CF$_3$: 2,7-Diiodo-9,9-dihexylfluorene (0.3635 g; 0.1898 mmol) and 2-(1,1,2,2-tetrmethylethyleneboronato)-9-(3,5-bistrifluoromethyl)phenyl-9-(4-hydroxy)phenylfluorene (0.25 g; 0.4176 mmol) were added to 25 ml of toluene, 1 ml of 40% tetraethylammonium hydroxide, and 1 ml of water. The mixture was degassed with argon for 20 minutes. Then tetrakis-triphenylphosphine palladium(0) (0.0225 g; 0.019 mmol) was added and the mixture was stirred under a positive nitrogen pressure at 75° C. for 24 hours. The cooled mixture was diluted with 20 ml of 1N HCl and stirred for 10 minutes then filtered through CELITE®. The aqueous phase was discarded and the organic phase was washed successively with equal volumes of water (3×) and brine (1×). The solution was then passed through a fritted filter containing a 5-10 mm layer of 3-(diethylenetriamino)propyl-functionalized silica gel and anhydrous CaSO$_4$. Removal of solvent in vacuo afforded a residue that was chromatographed on silica gel (eluting with 0-50% EtOAc/hexanes) to afford 0.3 g of the desired product as a gum in 61% yield.

Example 11

Synthesis of phenol end-capped compound (VIa) with Ar=2,5-diphenyl-1,3,4-oxadiazole-4,4'-diyl, n=1, R=t-Bu, R'=H: The compound was prepared using procedures similar to those described herein. Mass spectral data were in agreement with the structure of the desired compound.

Example 12

Synthesis of phenol end-capped compound (VIa) with Ar=anthracene-9,10-diyl, n=1, R=t-Bu, R'=H: The compound was prepared using procedures similar to those described herein. Mass spectral data were in agreement with the structure of the desired compound.

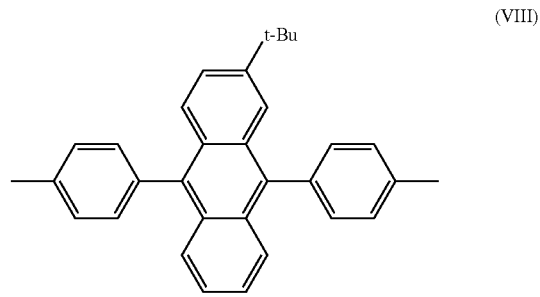

(VIII)

Example 13

Synthesis of phenol end-capped compound (VIb) with Ar=3-t-butyl-9,10-diphenylanthracene-4,4'-diyl structure (VIII), n=1, R=H, R'=CF$_3$: The compound was prepared using procedures similar to those described herein.

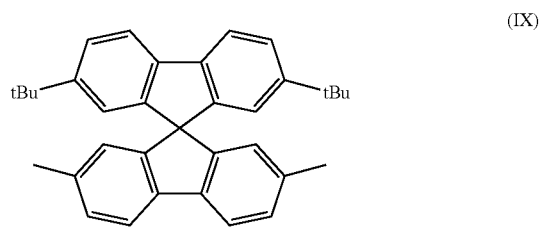

(IX)

Example 14

Synthesis of phenol end-capped compound (VIb) with Ar=spiro-bis-fluorenyl structure (IX), n=1, R=H, R'=CF$_3$: The compound was prepared using procedures similar to those described herein. Mass spectral data were in agreement with the structure of the desired compound.

Example 15

Synthesis of alternating polycarbonates (Xb) with Ar=9,9-dihexylfluorene-2,7-diyl, R=H, R'=CF$_3$ and (Xa) with Ar-9,9-dihexylfluorene-2,7-diyl, R=t-Bu, R'=H from fluorene oligomer bis-phenols and bisphenol-A-bis-chloroformate:

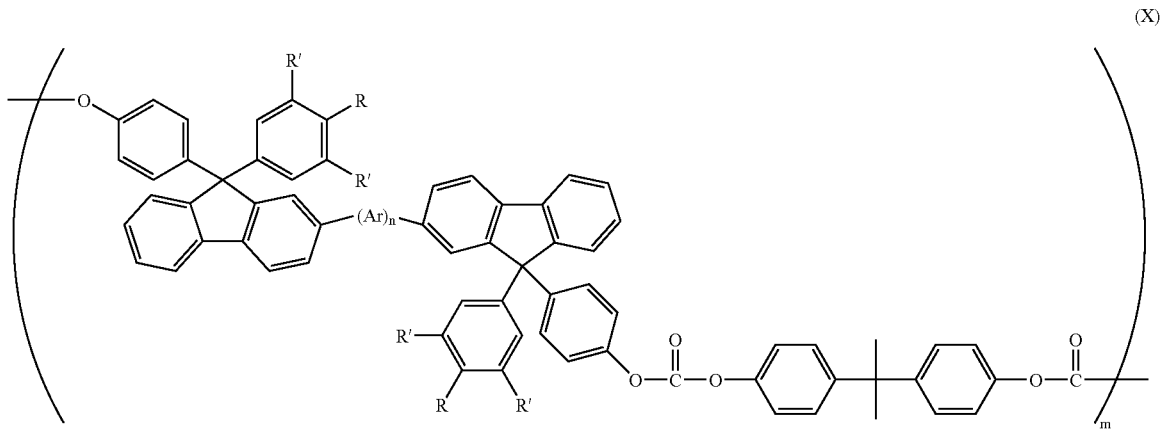

(X)

20

A dry reaction vessel equipped with a magnetic stirring bar and a septum fitted with a syringe leading to a dry nitrogen bubbler was charged with the phenol end-capped heptafluorene compound (VIb) with n=5 (178.2 mg; 0.0685 mmol), bisphenol-A bis-chloroformate (24.2 mg; 0.0685 mmol) and 1.5 ml of dry $CH_2Cl_2$. The resulting solution was immersed in an ice-salt bath for 15 minutes and then charged with 25 microliters (0.179 mmol) of dry triethylamine. The mixture was maintained at 0-5° C. with stirring for 1 hour then allowed to warm to room temperature and stirred for an additional hour. Then the mixture was diluted with 1.0 ml of $CH_2Cl_2$, followed by addition of 1.0 ml of 10% $NaHCO_3$. The mixture was stirred for 10 minutes and then transferred to a separatory funnel. The aqueous phase was discarded and the organic phase was washed successively with equal volumes of 1 N HCl (1×) and water (2×). The solution was concentrated to about ⅔ its original volume and then precipitated into 40 ml of methanol. The collected polymer was redissolved in $CH_2Cl_2$ and this solution was added slowly to 100 ml of boiling, deionized water. The solids were again collected, air-dried, redissolved in fresh $CH_2Cl_2$ and reprecipitated again into 50 ml of methanol. The resulting polymer was dried at 50° C. in a vacuum oven for 18 hrs. Molecular weight, as determined by gel permeation chromatography, was found to be as follows: weight average molecular weight 56,200; number average molecular weight 24,300; polydispersity index 2.31. Other polycarbonates were prepared similarly. Pertinent characterization data are presented in Table 1. The abbreviation "Eg" means energy gap; the abbreviation "CV" means cyclic voltammetry.

Example 16

The solubility properties of the polymer Xa (n=1) were compared with a commercially available polyfluorene and are shown in the table 2 below. The commercially available polyfluorene was poly(9,9-dioctylfluorenyl-2,7-diyl) end capped with N,N-bis(4-methylphenyl)-4-aniline (ADS-329; obtained from American Dye Source), and was used as received. The solubility tests were conducted by taking the polymer in a vial with the solvent at comparable concentration of 1-5 weight percent with respect to the solvent and stirring at room temperature for 24 hours. The solubility characteristics were classified as soluble, partially soluble, swelling and insoluble. Table 2 shows that polymers of the invention showed improved solubility characteristics as compared to the commercially available polymer.

TABLE 2

| Solvent | Comparative Example | Polymer Xa (n = 1) |
|---|---|---|
| Chloroform | Soluble | Soluble |
| Xylenes | Partially Soluble | Soluble |
| Cumene | Partially soluble | Soluble |
| Propylenecarbonate | Swelling | Swelling |
| Glyme | Insoluble | Soluble |
| Ethyl Acetate | Insoluble | Soluble |
| Heptanes | Insoluble | Insoluble |

TABLE 1

| Polymer | Mw (×10³ Daltons) | Mn (×10³ Daltons) | Mw/Mn | UVmax eV | Eg (uv) eV | HOMO (CV) | LUMO (CV) | Eg (CV) |
|---|---|---|---|---|---|---|---|---|
| Xb(n = 0) | 29.9 | 10.3 | 2.9 | 3.75 | 3.36 | 5.86 | 2.55 | 3.40 |
| Xb(n = 1) | 50.8 | 15.3 | 3.31 | 3.49 | 3.14 | 5.71 | 2.47 | 3.24 |
| Xb(n = 3) | 15.2 | 7.6 | 1.99 | 3.34 | 3.05 | 5.69 | 2.38 | 3.31 |
| Xb(n = 5) | 56.2 | 24.3 | 2.31 | 3.29 | 3.02 | 5.69 | 2.34 | 3.35 |
| Xa(n = 0) | 42.9 | 9.3 | 4.61 | 3.75 | 3.35 | 5.92 | 2.17 | 3.75 |
| Xa(n = 1) | 18.9 | 9.2 | 2.05 | 3.49 | 3.10 | 5.61 | 2.18 | 3.43 |

TABLE 2-continued

| Solvent | Comparative Example | Polymer Xa (n = 1) |
|---|---|---|
| Acetonitrile | Insoluble | Insoluble |
| Water | Insoluble | Insoluble |

Example 17

Synthesis of alternating polycarbonate (Xa) with Ar=2,5-diphenyl-1,3,4-oxadiazole-4,4'-diyl, R=t-Bu, R'=H from fluorene oligomer bis-phenol and bisphenol-A-bis-chloroformate: The polymer was prepared using procedures similar to those described herein. Molecular weight, as determined by gel permeation chromatography, was found to be as follows: weight average molecular weight 28,547; number average molecular weight 12,309; polydispersity index 2.32.

Example 18

Synthesis of alternating polycarbonate (Xa) with Ar=anthracene-9,10-diyl, R=t-Bu, R'=H from fluorene oligomer bis-phenol and bisphenol-A-bis-chloroformate: The polymer was prepared using procedures similar to those described herein. Molecular weight, as determined by gel permeation chromatography, was found to be as follows: weight average molecular weight 31,942; number average molecular weight 13,420; polydispersity index 2.38.

Example 19

Synthesis of alternating polycarbonate (Xb) with Ar=3-t-butyl-9,10-diphenylanthracene-4,4'-diyl structure (VIII), n=1, R=H, R'=CF$_3$ from fluorene oligomer bis-phenol and bisphenol-A-bis-chloroformate: The polymer was prepared using procedures similar to those described herein. UV (max) in CH$_2$Cl$_2$ 400 nm, 378 nm, 359 nm (anthracene), and 300 nm. Molecular weight, as determined by gel permeation chromatography, was found to be as follows: weight average molecular weight 10,000; number average molecular weight 5,600; polydispersity index 1.78. NMR data were in agreement with the structure of the desired compound.

Example 20

Synthesis of alternating polycarbonate (Xb) with Ar=spiro-bis-fluorenyl structure (IX), n=1, R=H, R'=CF$_3$ from fluorene oligomer bis-phenol and bisphenol-A-bis-chloroformate: The polymer was prepared using procedures similar to those described herein. UV (max) in CH$_2$Cl$_2$ 355 nm; molecular weight, as determined by gel permeation chromatography, was found to be as follows: weight average molecular weight 21,000; number average molecular weight 10,400; polydispersity index 2.02.

Example 21

Synthesis of polycarbonate (Xa) with R=t-Bu, R'=H from fluorene oligomer bis-phenol, bisphenol A, and phosgene: Reaction of phenol end-capped terfluorene compound (VIa) with n=1 with phosgene and bisphenol A afforded the corresponding polycarbonate. Molecular weight, as determined by gel permeation chromatography, was found to be as follows: weight average molecular weight 35,818; number average molecular weight 15,273; polydispersity index 2.34.

Example 22

Synthesis of statistical oligomer, compound (XI):

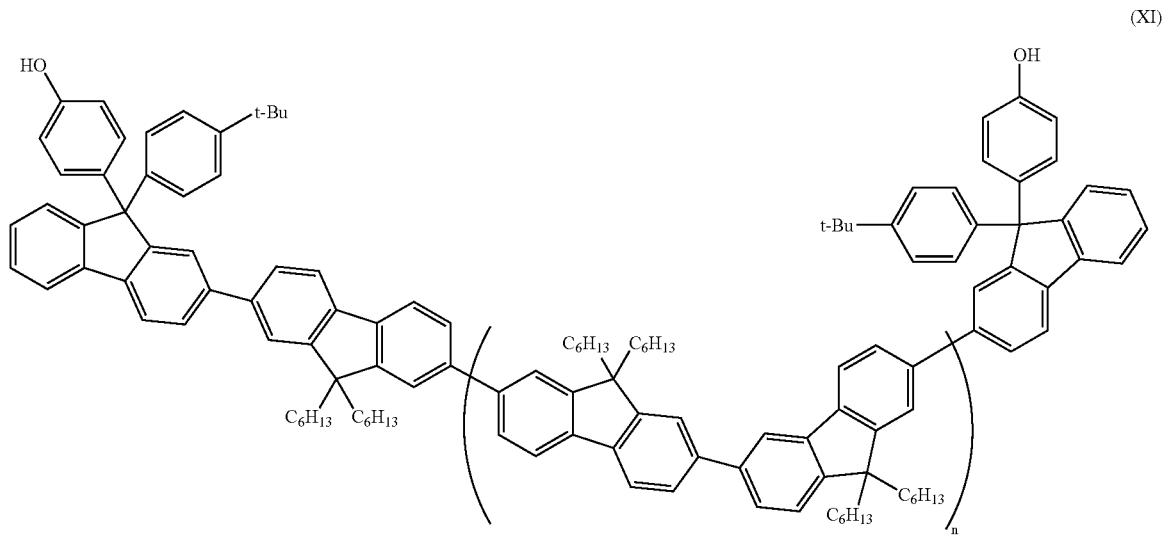

(XI)

A mixture of 9,9-dihexylfluorene-2,7-bis-trimethyleneborate (0.301 g; 0.6 mmol), 2,7-dibromo-9,9-dihexylfluorene (0.197 g; 0.4 mmol), compound (IVa) (0.220 g; 0.4 mmol), tetraethylammonium hydroxide, (1.0 ml of a 20% aqueous solution) and 15 ml of toluene was degassed with argon for 20 minutes. Then tetrakis-triphenylphosphine palladium(0) (0.03 g; 0.026 mmol) was added, and the mixture was stirred under a positive nitrogen pressure and immersed in a 75° C. bath for 3 hours. The cooled mixture was diluted with 25 ml of 1N HCl and stirred for 10 minutes then filtered through CELITE®. The aqueous phase was discarded and the organic phase was washed successively with equal volumes of water (3×) and brine (1×). The solution was then passed through a fritted filter containing a 5-10 mm layer of 3-(diethylenetriamino)propyl-functionalized silica gel and anhydrous CaSO$_4$, and then stripped to afford a tan solid that was dissolved in CH$_2$Cl$_2$ and precipitated into methanol. The collected solid was dried in a vacuum oven to afford about 0.4 g of the desired oligomer. The molecular weight was determined using $^{31}$P-NMR endgroup quantitation technique. The average degree of polymerization was estimated to be 8.50, and thus, M$_n$ was calculated to be 3761. MALDI-TOF mass spectrum was in agreement with the structure of the desired compound.

The following examples illustrate the synthesis of various kinds of polymers with the repeat unit of formula (XII):

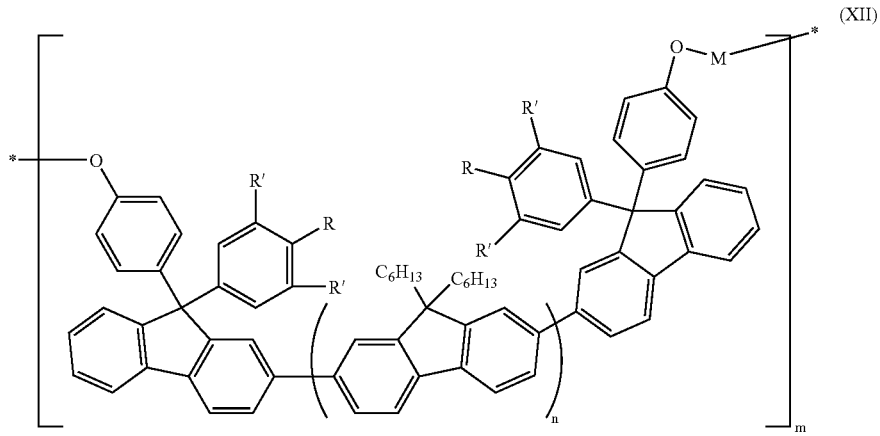

Example 23

Synthesis of polycarbonate (XIIa) with R=t-Bu, R'=H from fluorene oligomer bis-phenol and phosgene, wherein M=CO: Reaction of phenol end-capped terfluorene compound (VIa) with n=1 with one equivalent of phosgene in methylene chloride in the presence of a pH 10 buffer afforded approximately 80% yield of the corresponding polycarbonate. Molecular weight, as determined by gel permeation chromatography, was found to be as follows: weight average molecular weight 25,025; number average molecular weight 7,808; polydispersity index 2.96.

Example 24

Synthesis of polyether (XIIa with R=t-Bu, R'=H) from phenol end-capped terfluorene and 2,5-di-(4-fluoro)phenyl-1,3,4-oxadiazole, wherein:

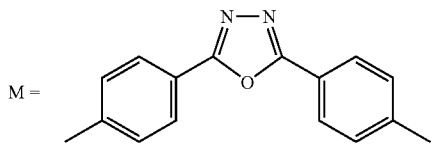

A 50 ml flask equipped with a magnetic stir bar, a distillation take-off and receiver and a nitrogen inlet, was charged with phenol end-capped terfluorene compound (VIa) with n=1 (0.471 g; 0.424 mmol), 2,5-di-(4-fluoro)phenyl-1,3,4-oxadiazole (0.109 g; 0.424 mmol), potassium carbonate (0.117 g; 0.848 mmol), N-methyl-2-pyrrolidinone (NMP; 3.0 ml) and toluene (10 ml). The flask was immersed in an oil bath and heated to remove toluene and water. When all of the toluene had been distilled, the bath temperature was raised to 170° C. and the reaction was maintained at that temperature for 3 hours. The cooled mixture solidified and was diluted with 5 ml each of CH$_2$Cl$_2$ and tetrahydrofuran (THF) and 10 ml of water. The resulting 2-phase slurry was poured slowly into 75 ml of methanol containing 2 ml of 1N HCl. The white solid polymer that separated was collected by filtration. After two precipitations from THF into methanol, the polymer was stirred overnight with a 60/40 methanol/acetone mixture, collected by filtration, and dried in a vacuum oven overnight. Molecular weight, as determined by gel permeation chromatography, was found to be as follows: weight average molecular weight 34,400, number average molecular weight 13,800, polydispersity index 2.60.

Example 25

Synthesis of polyether (XIIb with R=H, R'=CF$_3$) from phenol end-capped terfluorene and decafluorobiphenyl, wherein:

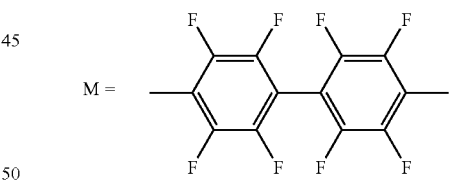

A 25 ml flask equipped with a magnetic stir bar, a distillation take-off and receiver and a nitrogen inlet was charged with phenol end-capped terfluorene compound (VIb) with n=1 (0.576 g; 0.519 mmol), decafluorobiphenyl (0.173 g; 0.519 mmol), potassium carbonate (0.148 g; 1.038 mmol), NMP (2.0 ml) and toluene (6 ml). The flask was immersed in an oil bath and heated to remove toluene and water. When all of the toluene had been distilled, the bath temperature was raised to 170° C. and the reaction was maintained at that temperature for 3 hours. The cooled mixture was diluted with 3 ml of CH$_2$Cl$_2$ and poured into 50 ml of rapidly stirring methanol. The residue was washed with methanol and air dried. It was subsequently redissolved in CH$_2$Cl$_2$ and filtered through a glass wool plug. This solution was added slowly to 75 ml of boiling water and the aqueous slurry was stirred overnight at room temperature, filtered and then the collected solids were dried in a vacuum oven. The dried polymer was re-dissolved in methylene chloride and precipitated into 50 ml of a 30/20-methanol/acetone mixture. After stirring in this mixture for 3 hours, the solids were collected by filtration and analyzed. Molecular weight, as determined by gel permeation chromatography, was found to be as follows: weight average molecular weight 96,600, number average molecular weight 27,900, polydispersity index 3.46.

Example 26

Synthesis of polymer (XIIa with R=t-Bu, R'=H) from phenol end-capped terfluorene and diphenylsilane, wherein:

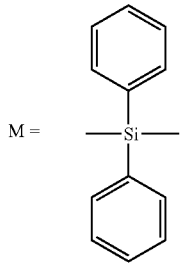

Phenol end-capped terfluorene, compound (VIa) with n=1 (0.555 g; 0.50 mmol) and diphenylsilane (0.092 g; 0.50 mmol) were dissolved in 1 ml of dry toluene. Tris-pentafluorophenylboron (0.0018 g; 0.0035 mmol) was added and the resulting mixture was stirred at 80° C. until gas evolution ceased (2 days). The solution was added to 25 ml of methanol and the white polymer powder was collected by filtration. The resulting product was dried in vacuo to yield 0.30 g.

Example 27

Synthesis of polymer (XIIa with R=t–Bu, R'=H) from phenol end-capped terfluorene and 1,1,3,3-tetramethyldisiloxane, wherein:

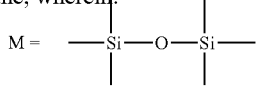

Phenol end-capped terfluorene compound (VIa) with n=1 (0.222 g; 0.0.20 mmol) and 1,1,3,3-tetramethyldisiloxane (0.0273 g; 0.204 mmol) were dissolved in 1.0 ml of dry toluene and tris-pentafluorophenylboron (0.0003 g; 0.00054 mmol) was added (27 microliters of a 0.10 g/10 ml toluene solution). When gas evolution ceased (about 2 hrs) solvent was removed under vacuum affording the polymer as a white powder. Molecular weight, as determined by gel permeation chromatography, was found to be as follows: weight average molecular weight 1288; polydispersity index 1.36.

Example 28

Synthesis of polyformal (XIIa with R=t-Bu, R'=H) from phenol end-capped terfluorene and methylene chloride, wherein:

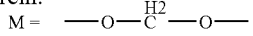

To a solution of phenol end-capped terfluorene compound (VIa) with n=1 (1.185 g; 1.067 mmol) and 4-cumylphenol (0.0034 g; 0.016 mmol) and excess methylene chloride (0.30 ml) in NMP (2.5 ml) was added dry, granular sodium hydroxide (0.085 g; 2.125 mmol). This mixture was stirred under a positive nitrogen pressure and heated at 75° C. for 18 hours. The cooled mixture was diluted with an additional 3 ml of NMP and filtered through CELITE®. To the filtrate was added 25 ml of a 1/1 methanol/acetone mixture. The precipitated solids were collected by filtration to afford the polyformal. Molecular weight, as determined by gel permeation chromatography, was found to be as follows: weight average molecular weight 6,173; polydispersity index 1.41.

Example 29

Synthesis of polyester (XIIa with R=t-Bu, R'=H) from phenol end-capped terfluorene and cyclohexane-1,4-dicarbonyl dichloride, wherein:

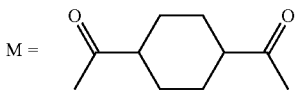

A 25 ml flask equipped with a nitrogen inlet was charged with phenol end-capped terfluorene compound (VIa) with n=1 (0.5 g; 0.45 mmol), cyclohexane-1,4-dicarbonyl dichloride (0.096 g; 0.46 mmol), and dry dichloromethane (10 ml). The flask was immersed in an ice/salt bath to reduce the reaction mixture temperature to less than 0° C. To this was added triethylamine (0.1 g; 0.99 mmol). The solution was stirred at 0° C. for 1 hour and was then allowed to warm to room temperature. Once the mixture reached room temperature, 4-(1-methyl-1-phenyl-ethyl)phenol (0.002 g; 0.01 mmol), was added. The reaction mixture was further diluted with 10 ml of dichloromethane and transferred to a separatory funnel. The solution was washed three times with an equal amount of 10% hydrochloric acid solution followed by three water washes. The organic phase was separated and concentrated to a volume of approximately 15 ml. The solution was precipitated in 15 ml of methanol. The material was then precipitated from dichloromethane into hot water and then reverse precipitated using acetone. The polymer was collected by vacuum filtration and dried in a vacuum oven overnight. Molecular weight, as determined by gel permeation chromatography, was found to be as follows: weight average molecular weight 49,900; number average molecular weight 8,900; polydispersity index 5.60.

Example 30

Synthesis of N-Phenylcarbazole-bis-phenol monomer (XIII):

(XIII)

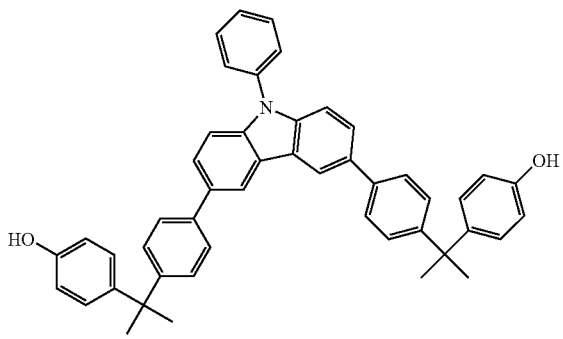

A mixture of 3,6-dibromo-N-phenylcarbazole, (0.5 g, 1.25 mmol), 2-(4-hydroxyphenyl)-2-(4-pinacolatoboraphenyl)propane, (0.927 g, 2.74 mmol), tetraethylammonium hydroxide, 2.5 ml of a 20% aqueous solution and toluene (25 ml) was purged with argon for 15 minutes then tetrakis-triphenylphosphine palladium(0), (0.032 g, 0.027 mmol) was added and the mixture was immersed in an oil bath and heated under a positive nitrogen pressure at 80° C. for 21 hours. The cooled mixture was diluted with approximately 20 ml of 10% HCl and approximately 10 ml of tetrahydrofuran, and this mixture was stirred for 30 minutes, filtered through CELITE® then transferred to a separatory funnel. The organic phase was washed with water (3×25 ml) and brine (1×25 ml) then filtered through a fritted glass funnel containing a short pad of CELITE® and about 1 g of amine-functional silica gel. Removal of solvent afforded 1.3 g of a dark amber oil that was chromatographed on 50 g of silica gel eluted with a hexane-ethyl acetate gradient. The product was isolated as a white solid.

Example 31

Synthesis of Cumylphenol-capped 9,9-dihexylfluorene oligomer (XIV):

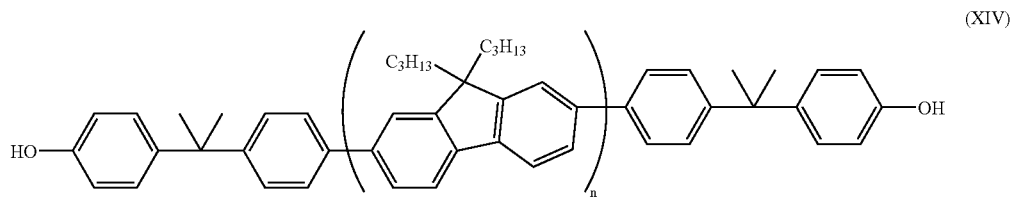

A solution of 2,7-dibromo-9,9-dihexylfluorene, (1.64 g; 3.33 mmol), 9,9-dihexylfluorene-2,7-bis-trimethyleneborate, (2.51 g; 5.00 mmol), 2-(4-hydroxyphenyl)-2-(4-bromophenyl)propane, (0.97 g; 3.33 mmol), tetraethylammonium hydroxide, (10 ml of a 20% aqueous solution), and tetrakis-triphenylphosphine palladium(0), (116 mg; 0.1 mmol) in toluene (75 ml), was degassed with argon for 20 minutes then immersed in a 100° C. oil bath. The mixture was stirred under nitrogen for 20 hours. The cooled mixture was stirred for 1 hour with 10% HCl then filtered through CELITE®. The organic phase was washed with water (2×50 ml) and brine (1×50 ml) then passed through a pad of amine-functional silica gel. Removal of solvent afforded 3.2 g of a yellow solid. $^1$H NMR integration of the OH (4.7 ppm) and alkyl resonances (2.15 ppm; 4H) indicates a number average molecular weight of 3451 for this oligomer.

Example 32

Synthesis of Copolymer (XV) derived from cumylphenol-capped oligomer and N-phenylcarbazole-bis-phenol

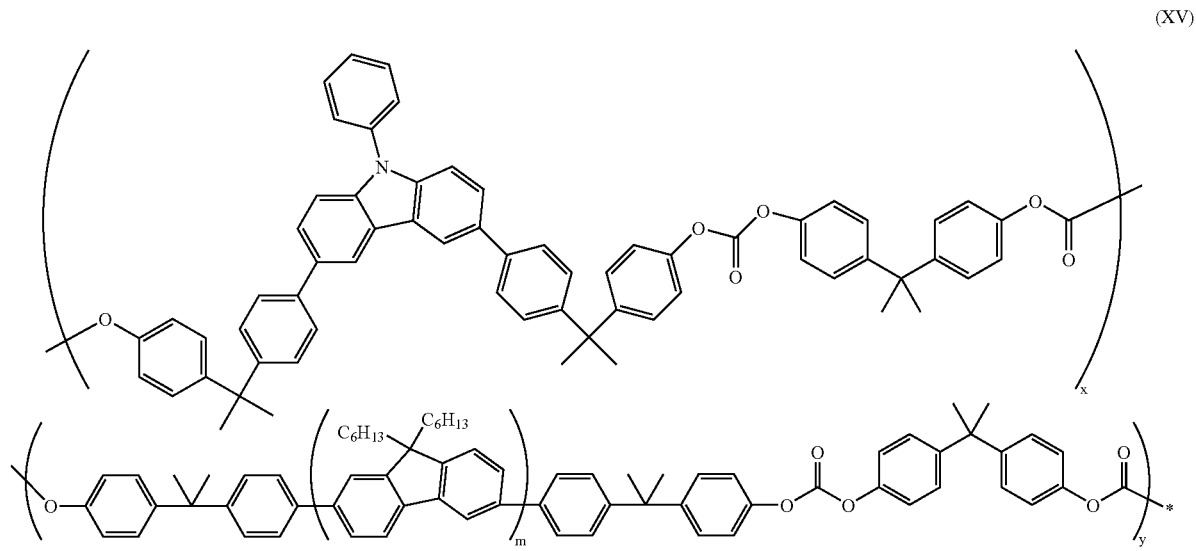

A solution of the oligomer described above, (0.876 g; 0.254 mmol), the carbazole-bis-phenol described above, (0.168 g; 0.254 mmol), p-cumylphenol, (4.3 mg; 0.02 mmol) and triethylamine, (0.150 ml; 1.08 mmol) in dry CH$_2$Cl$_2$ (12 ml) was chilled to about minus 5° C. in an ice-salt bath. To this solution was added at once bis-phenol-A bis-chloroformate, (0.183 g; 0.518 mmol). The mixture was stirred at minus 5° C. for 30 minutes then allowed to warm to room temperature over 1 hr. The contents were transferred to a separatory funnel and diluted with CH$_2$Cl$_2$ and water. The organic phase was washed with 10% HCl (1×) and water (2×), then concentrated on a rotary evaporator to about half its volume. This solution was added slowly to about 5 volumes of rapidly stirred methanol. The solids were collected by filtration to afford 1.0 g of polymer in 83% yield. The polymer was redissolved in CH$_2$Cl$_2$ and reprecipitated into 10% acetone/methanol. Molecular weight, as determined by gel permeation chromatography, was found to be as follows: weight average molecular weight 41,600; number average molecular weight 14,000.

Example 33

Synthesis of 0.75/0.25/1.0 copolymer from terfluorene-bis-phenol, N,N'-bis-4-hydroxyphenyl-N,N'-diphenyl-p-phenylenediamine and BPA (XVI):

ml of toluene was removed, the mixture was immersed in an ice-salt bath and triethylamine, (0.150 ml; 1.07 mmol) was added followed by BPA-bis-chloroformate, (0.176 g; 0.499 mmol). The mixture was stirred 1 hour at minus 5° C. and 2 hours at room temperature then transferred to a separatory funnel. The organic phase was washed with 10% HCl (1×) and water (2×) and was then precipitated into methanol. The collected polymer was redissolved in CH$_2$Cl$_2$ and reprecipitated into 1/1/1 methanol/isopropanol/acetone. Molecular weight, as determined by gel permeation chromatography, was found to be as follows: weight average molecular weight 168,000; number average molecular weight 66,000.

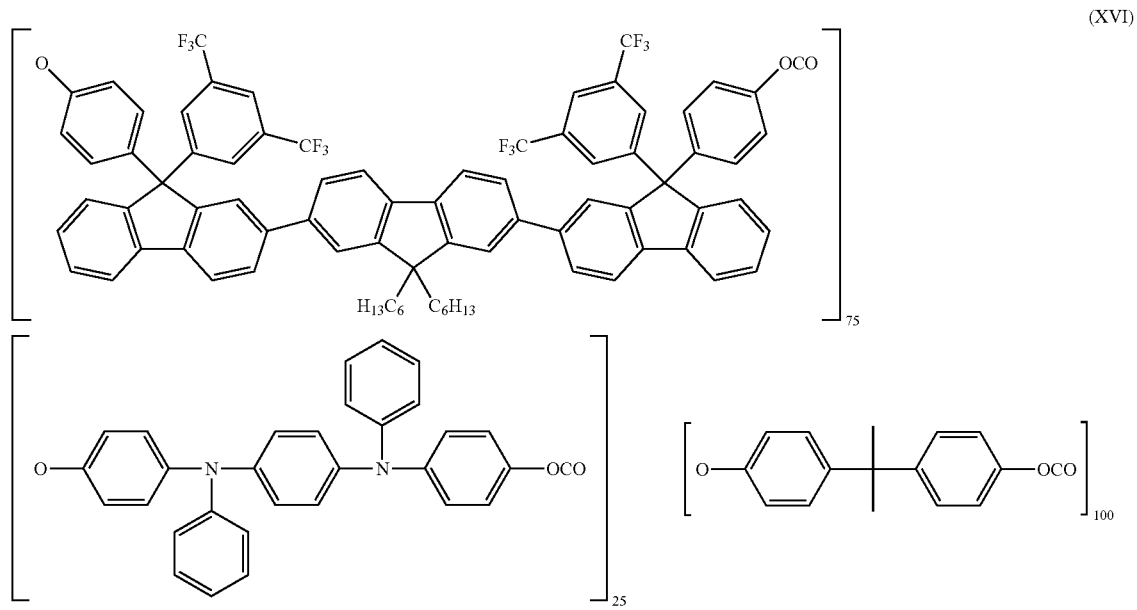

(XVI)

A solution of the terfluorene-bis-phenol (0.419 g; 0.3778 mmol) and N,N'-bis-4-hydroxyphenyl-N,N'-diphenyl-p-phenylenediamine (0.0559 g; 0.1259 mmol) in dry toluene (16 ml) was distilled to azeotropically dry the mixture. When 10

Example 34

Preparation of triarylamine bisphenol (XVII):

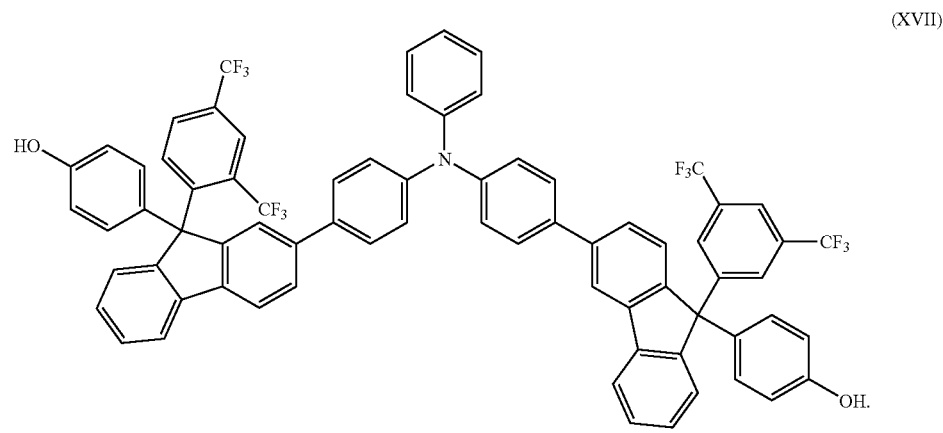

(XVII)

A mixture of 9-(3,5-bis-trifluoromethylphenyl)-9-(4-hydroxyphenyl)fluorene-2-boronic acid, (4.33 g; 9.975 mmol), N,N-bis-4-bromophenyl-N-phenylamine, (2.0 g; 4.988 mmol), tetraethylammonium hydroxide, (4.7 g of 40% aqueous solution), water (4.7 ml) and toluene (90 ml) was degassed for 20 minutes with argon then tetrakistriphenylphoshino palladium, (0.187 g, 0.16 mmol) was added and the mixture was immersed in an 80° C. oil bath. The mixture was stirred at this temperature under a positive nitrogen pressure for 2 days. The cooled mixture was stirred with dilute HCl (2%) for 1 hour, then filtered through CELITE®. The organic phase was washed with water (3×100 ml) and brine (1×100 ml) then passed through a short plug of mercapto-functional silica gel. Removal of solvent yielded a solid foamy mass that was crystallized from methylene chloride/hexane.

Example 35

Preparation of triphenylamine-bis-phenol-alt BPA-co-polycarbonate (XVIII):

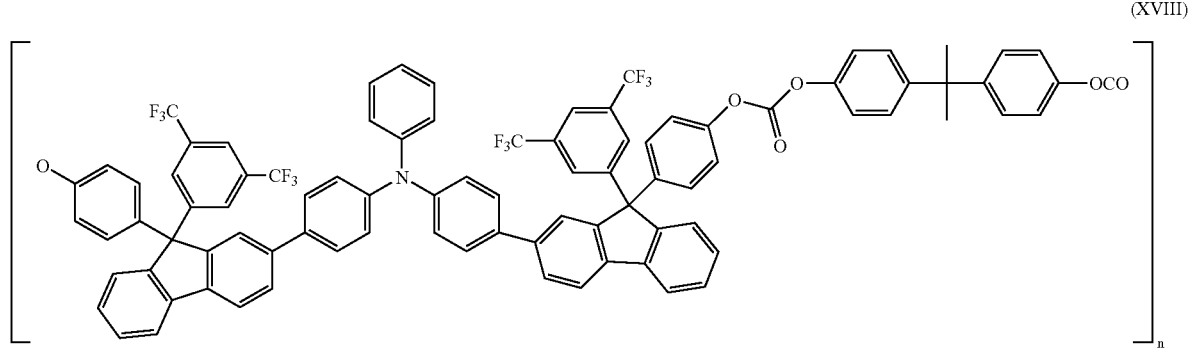

(XVIII)

A solution of the triarylamine-bis-phenol described above (0.200 g; 0.196 mmol), p-cumylphenol (0.0017 g, 0.08 mmol), and triethylamine (0.07 ml; 0.4 mmol) in dry $CH_2Cl_2$ (3 ml) was chilled to minus 5° C. in an ice-salt bath and BPA-bis-chloroformate, (0.0706 g; 0.200 mmol) was added at once. The mixture was stirred 1 hour at minus 5° C. then allowed to warm to room temperature. The mixture was diluted with $CH_2Cl_2$ and the organic phase was washed with 10% HCl (1×) and water (2×), then concentrated on a rotary evaporator and precipitated twice into methanol. Gel permeation chromatography indicates the material to be bimodal with the main peak (about 85% area) having a weight average molecular weight of about 25,000.

Device fabrication and measurement: For hole-only devices indium-tin-oxide (ITO) coated glass was cleaned, exposed to UV/ozone, coated with about 60 nanometer (nm) thick poly(3,4-ethylenedioxythiophene)-poly(styrenesulfonate) (PEDOT:PSS), baked, and then coated with the test polymer by spin-coating from a 2 wt. % solution in m-xylene. A shadow mask with eight 0.03 $cm^2$-large holes was used to vacuum-deposit top electrodes. For the hole-only samples an about 60 nm thick film of gold was evaporated at a rate or about 0.8 nm/sec. For the electron-only samples aluminum was used as the bottom electrode, and a thin layer of sodium fluoride plus aluminum for the top electrode. Several samples with different spin-speeds were made to allow to interpolate for a target value of 50 nm. Electrical contact was made with a thin gold wire mounted to a micro-probe. For the initial characterization a Textronix curve tracer was used, and then the I-Vs of the stable pixels were recorded with a standard source/measuring unit. The values reported are for the polarity corresponding to hole injection form the PEDOT contact, and electron injection from the top-contact.

For the bipolar results the structure was glass/ITO/PEDOT:PSS followed by a layer of about 65 nm thick light-emissive polymer, and a vacuum deposited cathode of 4 nm of sodium fluoride (NaF) and about 100 nm thick aluminum.

Electrochemistry: The solution used for electrochemical measurements was prepared by dissolving 0.1 M dry tetrabutylammonium tetrafluoroborate (98% min., GFS Chemicals) in acetonitrile (HPLC grade, J. T. Baker). Acetonitrile was distilled and freeze-dried before use. All cyclic voltammetric curves were obtained using a standard electrochemical setup consisting of a CH Instruments model 660A potentiostat and the three-electrode cell. The cell was placed in a glove-box (water below 1 ppm, oxygen below 2 ppm). A platinum disk (0.2 square centimeters ($cm^2$)) was polished with 1 micrometer alumina before every experiment and used as a working electrode. The polymeric films were deposited by spin coating at about 3000 rpm outside the glove-box. The reference electrode, Ag/Ag$^+$ (0.1 M AgNO$_3$ (99.9%, Alfa-Ventron) in acetonitrile) was calibrated vs. a Fc/Fc$^+$ (98%, Aldrich) electrode (0.017 V vs. Ag/Ag$^+$). Platinum mesh was used as a counter electrode. Voltammograms were recorded at 0.1 volts/second and always starting at the open circuit potential. The procedure to calculate HOMO and LUMO values from oxidation and reduction potentials respectively as described in S. Janietz et al., Appl. Phys. Lett. (1998), 73, 2453 was followed here also.

An organic light emitting device was fabricated in the following manner. An anode substrate comprising an indium tin oxide (ITO) layer was treated with ultraviolet ozone. This was then spin-coated with a 60 nm layer of poly(3,4)-ethylenedioxythiophene/polystyrene sulfonate (PEDOT/PSS). The coated anode substrate was then baked for 1 hour at 170° C. Subsequently, a layer of the test polymer was spin-coated over the PEDOT/PSS layer. A cathode layer comprising 4 nm of a NaF layer and 100 nm of aluminum was thermally deposited onto the anode substrate comprising the test polymer layer through a shadow mask. Finally, the fabricated device was encapsulated within glass slides and sealed with epoxy resin.

Figure 4:
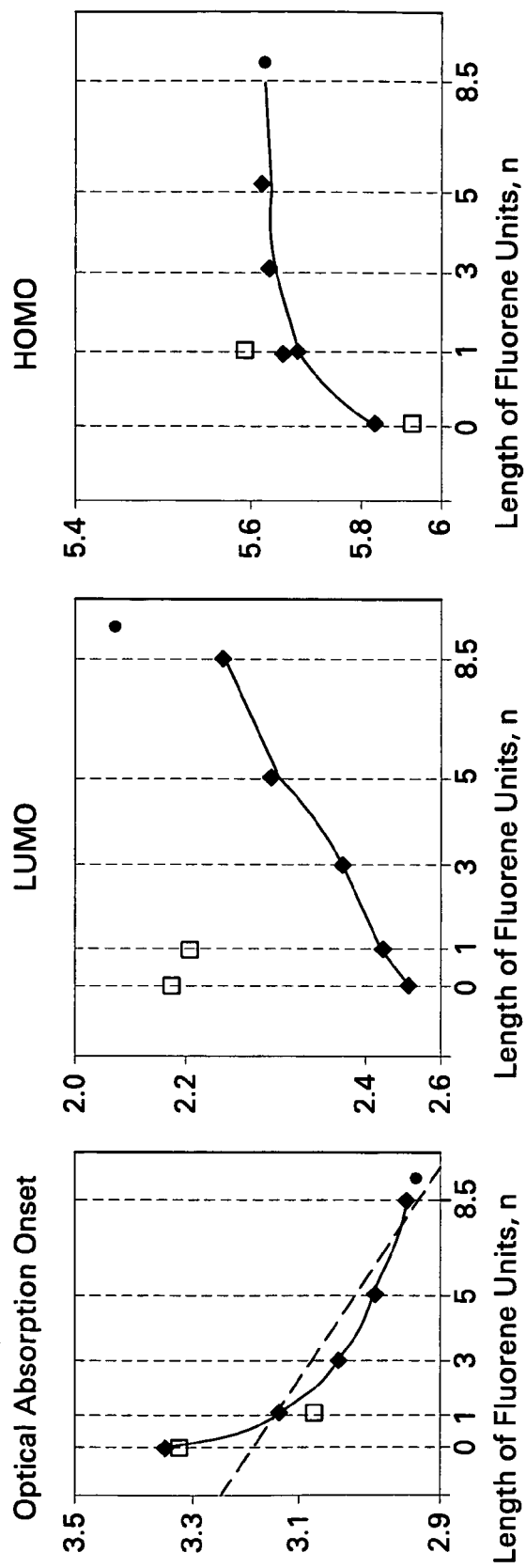
FIG. 4 shows properties for the test polymer (Xb) with n values of 0, 1, 3, 5, and 8.5 (filled-in diamonds), the test polymer (Xa) with n values of 0 and 1 (open squares), and a single control sample of poly(9,9-dihexylfluorene-2,7-diyl) homopolymer (filled-in circle). The properties shown are (a) optical absorption onset in methylene chloride; (b) the lowest unoccupied molecular orbital (LUMO); and (c) the highest occupied molecular orbital (HOMO) as a function of the length of fluorene (n) blocks.

FIG. 4 shows properties for the test polymer (Xb) with n values of 0, 1, 3, 5, and 8.5 (filled-in diamonds), the test polymer (Xa) with n values of 0 and 1 (open squares), and a single control sample of poly(9,9-dihexylfluorene-2,7-diyl)

homopolymer (filled-in circle). The properties shown are (a) optical absorption onset in methylene chloride; (b) the lowest unoccupied molecular orbital (LUMO); and (c) the highest occupied molecular orbital (HOMO) as a function of the length of fluorene (n) blocks. This figure demonstrates that the UV bandgaps for polymers of this invention are tunable by varying the conjugation length.

Figure 5:
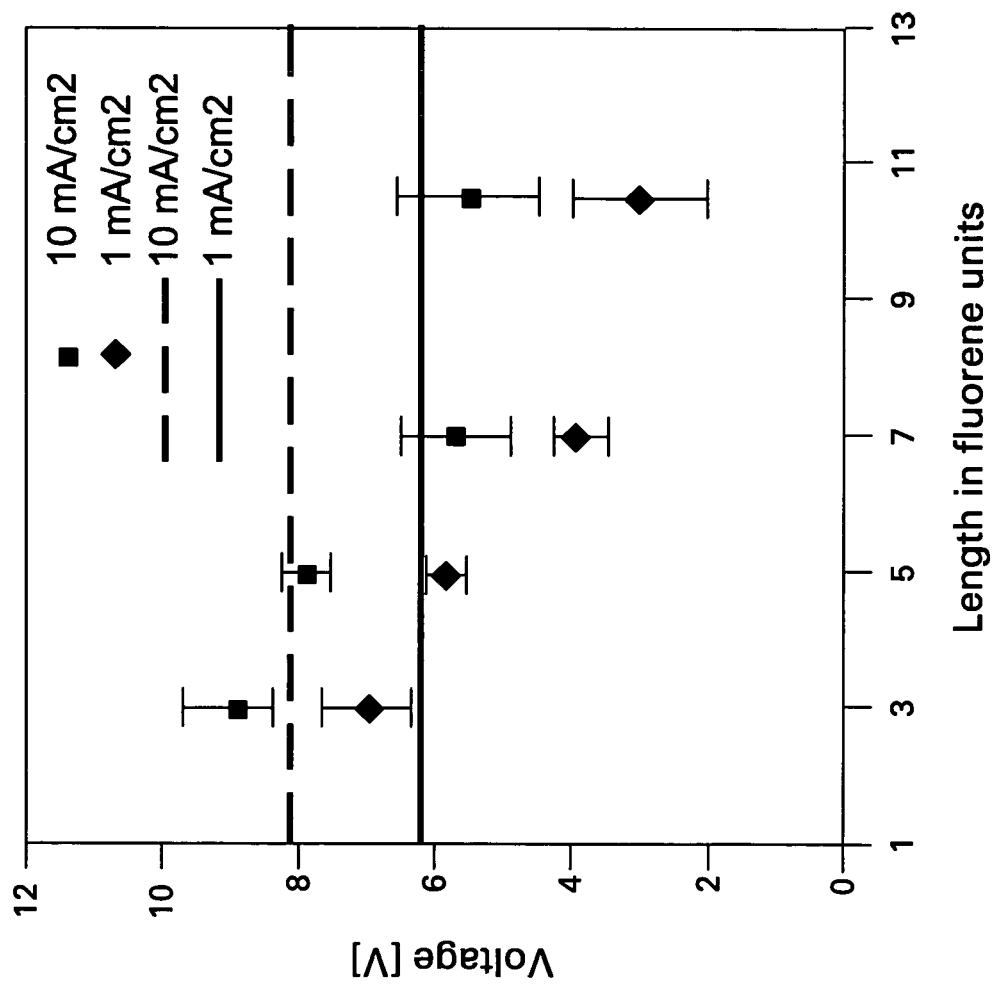
FIG. 5 shows the voltage at a current density of 1 mA/cm² (diamonds) and 10 mA/cm² (squares) for hole-only devices for 50 nm thick copolymer films comprising the alternating polycarbonate of formula (Xb) with the value for n corresponding to 3, 5, 7 and about 10.5 fluorene units. The two lines depict the voltages measured for a poly(9,9-dihexylfluorene-2,7-diyl) homopolymer: the dotted line represents the voltage measured at a current density of 10 mA/cm² while the solid line represents the voltage measured at a current density of 1 mA/cm².

FIG. 5 shows the voltage at a current density of 1 mA/cm$^2$ (diamonds) and 10 mA/cm$^2$ (squares) for hole-only devices for 50 nm thick copolymer films comprising the alternating polycarbonate of formula (Xb) with the value for n corresponding to 3, 5, 7 and about 10.5 fluorene units. The two lines depict the voltages measured for poly(9,9-dihexylfluorene-2,7-diyl) homopolymer: the dotted line represents the voltage measured at a current density of 10 mA/cm$^2$ while the solid line represents the voltage measured at a current density of 1 mA/cm$^2$. The figure clearly indicates that the carbonate-linked fluorene oligomers exhibit electroactive properties as good as or better than a polyfluorene homopolymer, and that polymers of this invention will serve as useful materials in electroactive devices.

Figure 6:
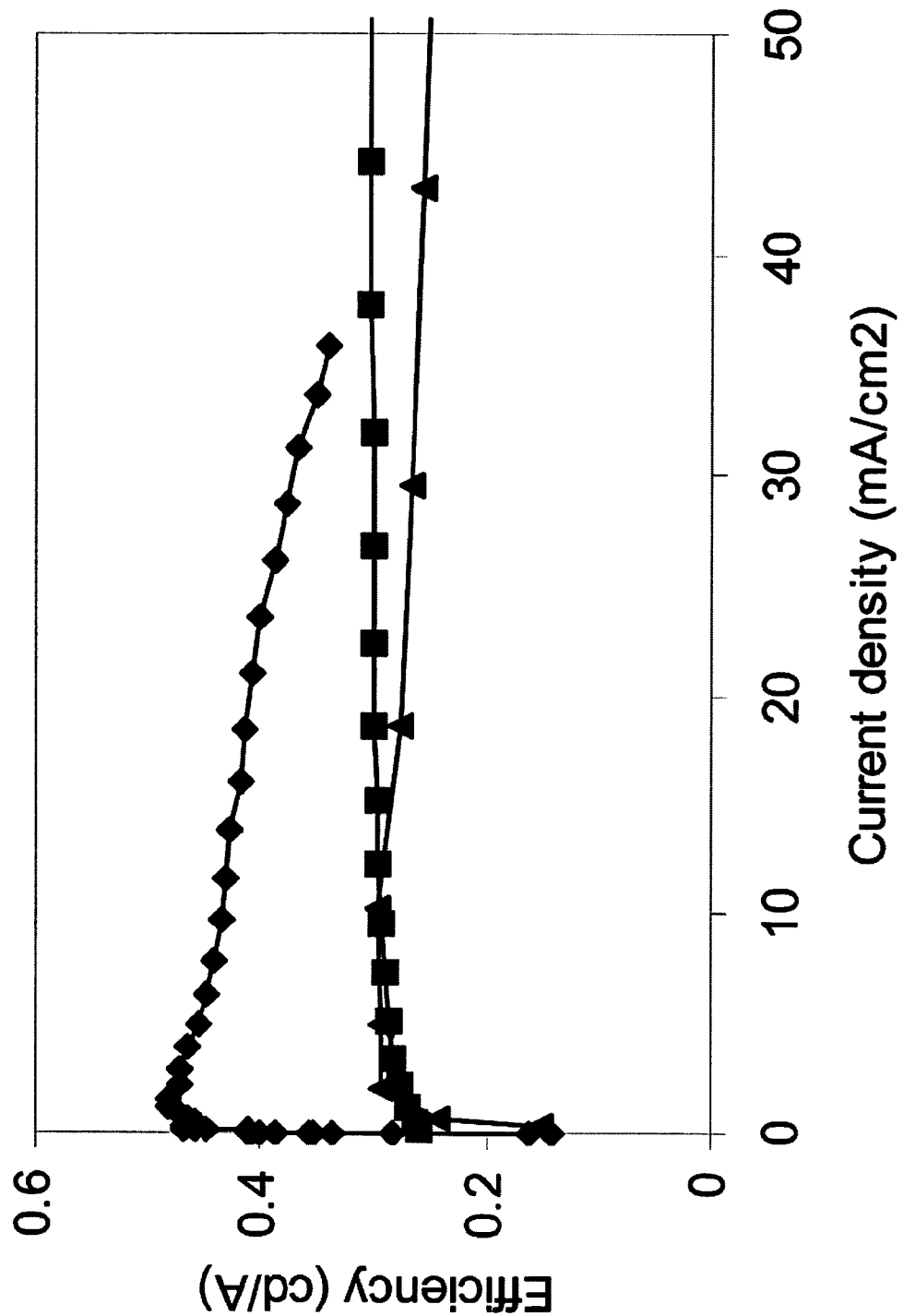
FIG. 6 shows the efficiency versus current density curves of OLEDs based on poly(9,9-dioctylfluorenyl-2,7-diyl) (square), poly[9,9-di-(2-ethylhexyl)-fluorenyl-2,7-diyl] (triangle) and polymer Xa (n=1) (diamond).

The efficiency of OLED devices was measured using one test polymer and two commercially available polymers as shown in FIG. 6. Polymers tested were: commercially available poly(9,9-dioctylfluorenyl-2,7-diyl) (square symbols in FIG. 6), commercially available poly[9,9-di-(2-ethylhexyl)-fluorenyl-2,7-diyl] (triangle symbols), and polymer Xa (n=1) (diamond symbols). The results are plotted in FIG. 6 which shows the efficiency versus current density curves for OLED devices comprising PEDOT/PSS polymer as an anode layer. Results shown in FIG. 6 demonstrate that the polymers of this invention are suitable for use in electroactive devices.

Preparation of dye-doped polymer films: Dopant solutions were prepared in toluene at a concentration of 2 mg/ml with the exception of the iridium complex, which was prepared at a concentration of 0.2 mg/ml of toluene due to its limited solubility. A stock solution of 10 mg/ml of polymer Xa (n=1) was prepared in m-xylene. The polymer Xa (n=1) solution was divided into 250 microliter portions and to each portion 10 microliter of the 2 mg/ml dye solution was added (100 microliter in the case of the Ir complex). These solutions were thoroughly mixed and drop cast on to a quartz plate. The weight loading of dye of the dried film was 0.8% (w/w) (0.02 mg dye per 2.5 mg host). The structures of the dopants used are as follows:

XIX: 7-Diethylamino-4-methylcoumarin

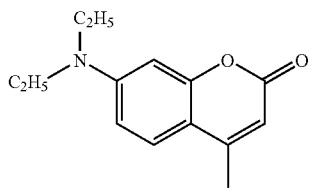

XX: 2,3,5,6-1H,4H-Tetrahydro-8-methylquinolizino-[9,9a,1-gh]-coumarin

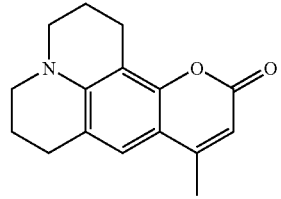

XXI: Bis(1-phenylisoquinoline)-(acetylacetonate) iridium (III)

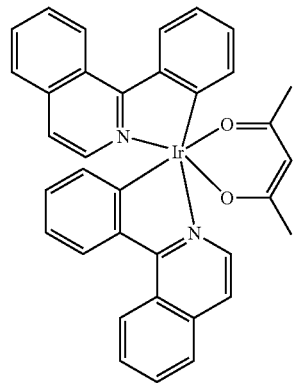

XXII: Tris(dinapthoylmethane)-mono(phenanthroline)europium(III)

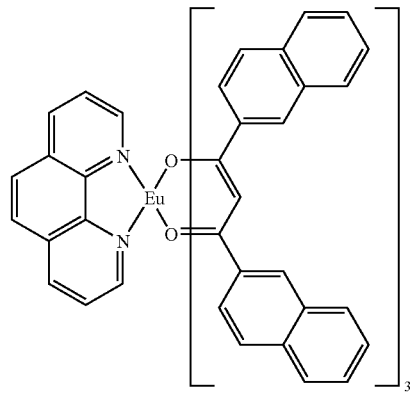

Figure 7:
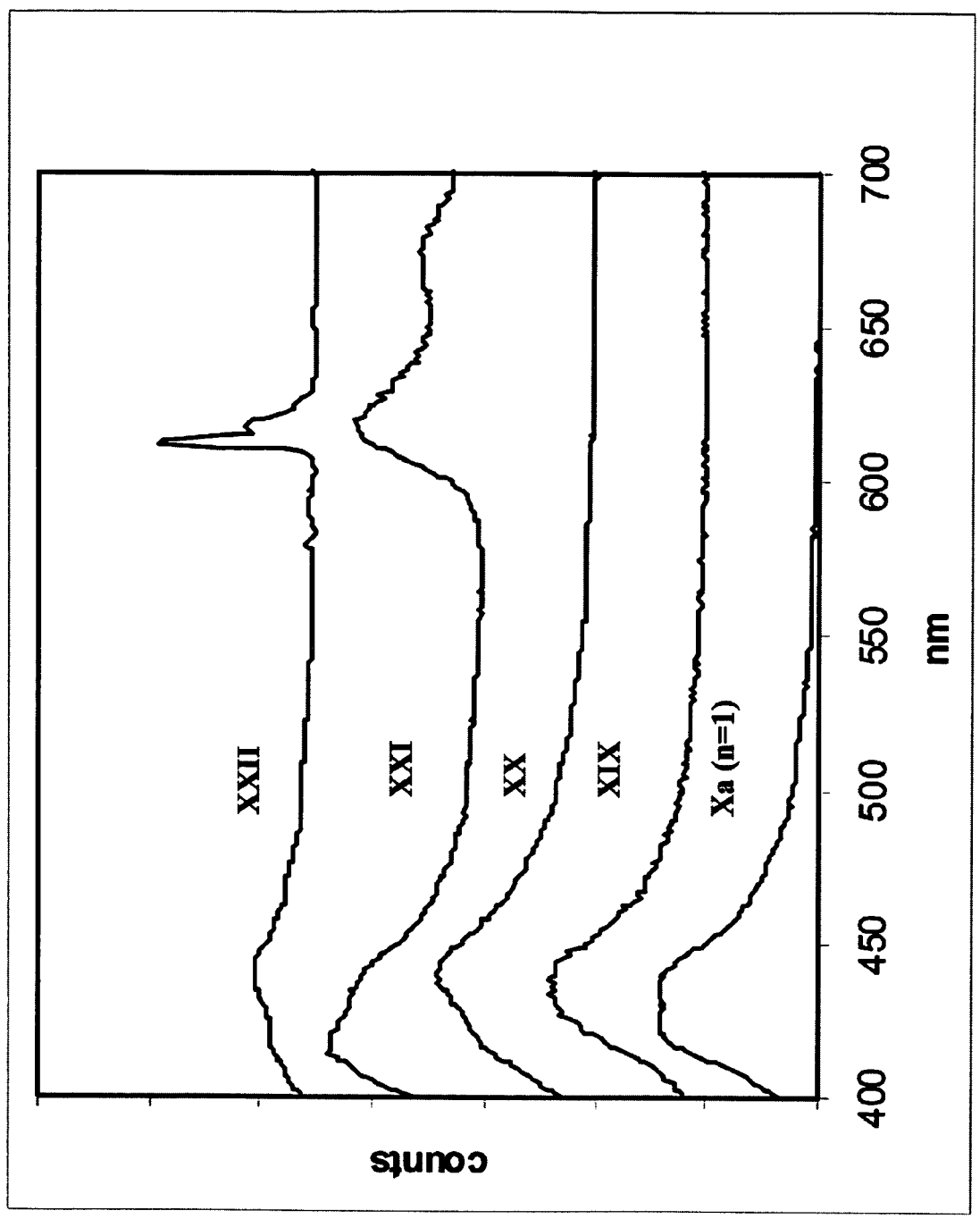
FIG. 7 shows the emitted luminescence due to excitation for electroactive devices comprising polymer Xa (n=1) blended with various dyes.

FIG. 7 shows the emitted luminescence (counts versus wavelength) of individual electroactive devices comprising polymer Xa (n=1) blended with dyes. Emission from both the polymer and the dye is evident here. Various transitions of the electrons in the excited spin state to the ground spin state in the dyes are responsible for the emissions that are observed. Some of the exemplary transitions include, but are not limited to singlet-singlet, singlet-triplet, triplet-triplet, quintet-septet, and the like. Table 3 shows transitions that may be responsible for photoluminescence of films comprising polymer with various dyes. Results shown here clearly demonstrate that the polymers of this invention are suitable hosts for fluorescent or phosphorescent dyes.

TABLE 3

| Dye Used | Transition (excited spin state to ground spin state) |
| --- | --- |
| None | Singlet - Singlet |
| XIX | Singlet - Singlet |
| XX | Singlet - Singlet |
| XXI | Triplet - Singlet |
| XXII | Quintet- Septet |

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All Patents and published articles cited herein are incorporated herein by reference.

The invention claimed is:

1. A composition comprising a polymer having structural units derived from the reaction of
a compound of formula

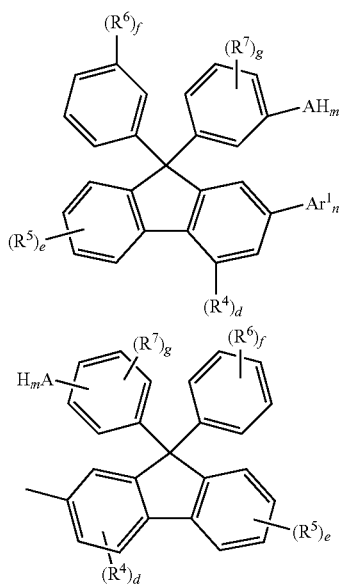

and at least one difunctional, organic monomer capable of reacting with the moiety $AH_m$ to form a polycarbonate, polyester, polyether, polyformal or polysiloxane homopolymer or copolymer;

wherein $R^2$, $R^3$, $R^4$, $R^5$, $R^6$, and $R^7$ are independently in each instance, an aliphatic, an aromatic or a cycloaliphatic radical;
A is O, N or S;
b is an integer having a value 0, 1, or 2;
c is an integer having a value ranging from 0 to 3;
d is an integer having a value ranging from 0 to 3;
e is an integer having a value ranging from 0 to 4;
f is an integer having a value ranging from 0 to 5;
g is an integer having a value ranging from 0 to 4;
m is 1 or 2;
n ranges from 0 to 100; and
$Ar^1$ is selected from

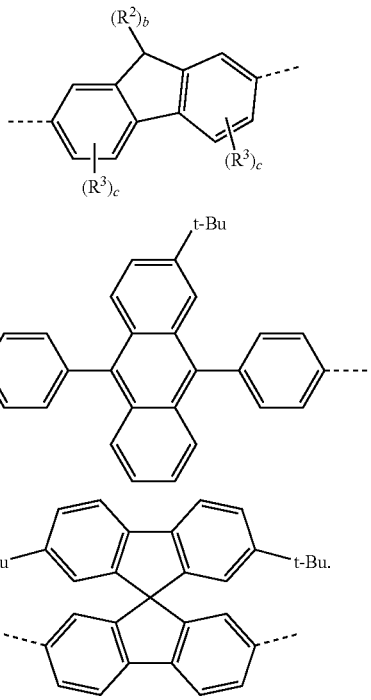

2. The composition of claim 1, wherein the polymer additionally comprises structural units derived from at least one compound of formula

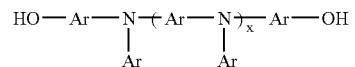

wherein Ar is independently in each instance an aromatic radical; 'x' are in each instance an integer ranging from 0 to 10;

or those of the formula:

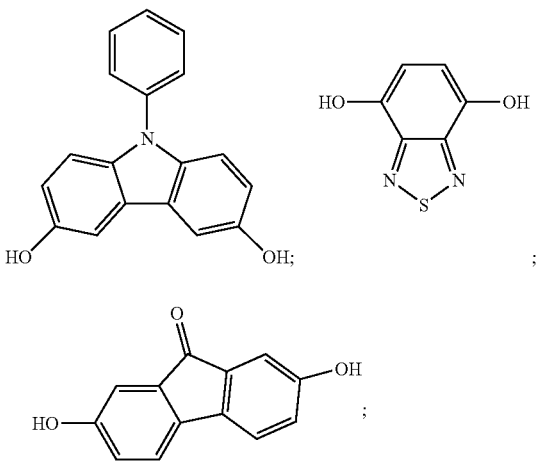

3. The composition of claim 1, herein the polymer comprises reactive end groups.

4. The composition of claim 3, herein the polymer comprises alcohol end groups, phenol end groups, acyl chloride end groups, aromatic halide end groups, aliphatic halide end groups, hydridosilane end groups, and combinations thereof.

5. The composition of claim 1, further comprising at least one additional polymer selected from the group consisting of poly(thiophene), poly(fluorene), poly(aniline), poly(phenylene), and poly(vinyl phenylene).

6. The composition of claim 1, wherein the composition further comprises at least one dye.

7. The composition of claim 6, wherein the dye comprises a perylene dye; an anthracene dye; a coumarin dye; 7-diethylamino-4-methylcoumarin; 2,3,5,6-1H,4H-tetrahydro-8-methylquinolizino-[9,9a, 1-gh]-coumarin; a stibene dye; a xanthene dye; an oxazine dye; a pyromethane dye; a 4-dicyanmethylene-2-methyl-6-(p-dimethylaminostyryl)-4H-pyran dye; a porphyrinoid dye; a dye comprising a metal complex of a porphyrinoid compound; a dye comprising an organic complex of a metal in the lanthanide series having an oxidation state of +2, +3, or +4; tris(dinapthoylmethane)-mono(phenanthroline)europium(III); a dye comprising an organic complex of a transition metal; a dye comprising at least one of Os, Ir, Ru, Rh, or Re; bis(1-phenylisoquinoline)-(acetylacetonate) iridium(III); or a combination of any of the aforementioned dyes.

8. The composition of claim 1, wherein the band gap is tunable by the variation of the conjugation length.

9. The composition of claim 1 herein the polymer is dissolved in a solvent.

10. An electroactive layer comprising the composition of claim 1.

11. An electroactive layer comprising the composition of claim 6.

12. A light emitting device comprising the electroactive layer of claim 10.

13. A light emitting device comprising the electroactive layer of claim 11.

14. A photovoltaic device comprising an electroactive layer, wherein said electroactive layer is formed from the composition of claim 1.

15. The composition of claim 1 herein n is between 0 and 5.

* * * * *

UNITED STATES PATENT AND TRADEMARK OFFICE
CERTIFICATE OF CORRECTION

PATENT NO. : 7,652,126 B2
APPLICATION NO. : 11/170423
DATED : January 26, 2010
INVENTOR(S) : Cella et al.

Page 1 of 1

It is certified that error appears in the above-identified patent and that said Letters Patent is hereby corrected as shown below:

In Column 7, Line 49, delete "$NO_2CH_2C_6H$ —)," and insert -- $NO_2CH_2C_6H_{10}$-), --, therefor.

In Column 7, Line 52, delete "$SiCH_2CH_2C_6H$ —)," and insert -- $SiCH_2CH_2C_6H_{10}$-), --, therefor.

In Columns 31-32, Equation (XIV) should appear as follows:

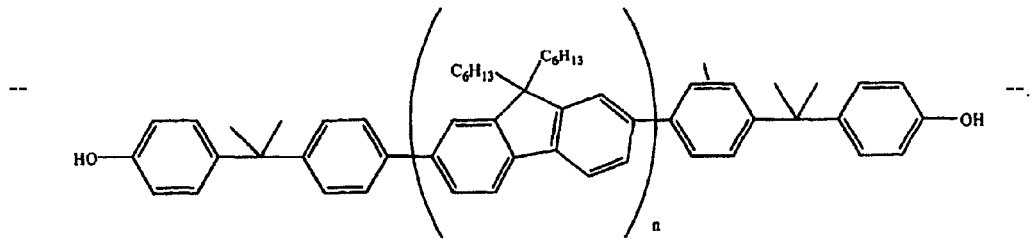

In Column 41, Line 42, in Claim 3, delete "herein" and insert -- wherein --, therefor.

In Column 42, Line 1, in Claim 4, delete "herein" and insert -- wherein --, therefor.

In Column 42, Line 28, in Claim 9, delete "herein" and insert -- wherein --, therefor.

In Column 42, Line 41, in Claim 15, delete "herein" and insert -- wherein --, therefor.

Signed and Sealed this

Thirteenth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,652,126 B2  Page 1 of 1
APPLICATION NO. : 11/170423
DATED : January 26, 2010
INVENTOR(S) : Cella et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 845 days.

Signed and Sealed this

Twenty-eighth Day of December, 2010

David J. Kappos
*Director of the United States Patent and Trademark Office*